United States Patent
Kondoh et al.

(10) Patent No.: US 7,563,548 B2
(45) Date of Patent: Jul. 21, 2009

(54) AMINE COMPOUND, MANUFACTURING METHOD THEREOF, ELECTROPHOTOGRAPHIC PHOTORECEPTOR USING AMINE COMPOUND AND IMAGE FORMING APPARATUS HAVING THE SAME

(75) Inventors: Akihiro Kondoh, Nara (JP); Takatsugu Obata, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 405 days.

(21) Appl. No.: 10/999,194

(22) Filed: Nov. 30, 2004

(65) Prior Publication Data

US 2005/0238972 A1 Oct. 27, 2005

(30) Foreign Application Priority Data

Dec. 1, 2003 (JP) ............ P2003-401638

(51) Int. Cl.
*G03G 5/06* (2006.01)
(52) U.S. Cl. .............. 430/58.85; 430/72; 430/73; 430/75; 430/79; 564/305; 564/431; 564/433; 564/435; 548/440; 549/74
(58) Field of Classification Search ............. 430/58.85, 430/72, 73, 79, 75; 564/305, 431, 433, 435; 549/74; 548/440
See application file for complete search history.

(56) References Cited

U.S. PATENT DOCUMENTS

| | | | |
|---|---|---|---|
| 3,824,099 A | 7/1974 | Champ et al. | |
| 4,123,269 A | 10/1978 | Von Hoene et al. | |
| 4,150,987 A | 4/1979 | Anderson et al. | |
| 4,278,747 A | 7/1981 | Murayama et al. | |
| 4,338,388 A | 7/1982 | Sakai et al. | |
| 4,367,273 A | 1/1983 | Murayama et al. | |

(Continued)

FOREIGN PATENT DOCUMENTS

EP 795791 A1 * 9/1997

(Continued)

OTHER PUBLICATIONS

English translation of JP 09-022130.*

(Continued)

*Primary Examiner*—Christopher RoDee
(74) *Attorney, Agent, or Firm*—Nixon & Vanderhye P.C.

(57) ABSTRACT

An amine compound represented by the general formula (1), which is incorporated as a charge-transporting substance to a charge-transporting layer of an electrophotographic photoreceptor:

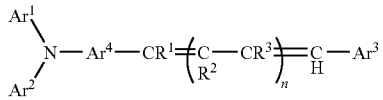

(1)

(in which $Ar^1$, $Ar^2$ and $Ar^3$ each represents an optionally-substituted aryl group, or an optionally-substituted monovalent heterocyclic ring residue. $Ar^4$ represents an optionally-substituted arylene group, or an optionally-substituted bivalent heterocyclic ring residue. $R^1$ represents an optionally-substituted alkyl group, an optionally-substituted aryl group, an optionally-substituted monovalent heterocyclic ring residue, or an optionally-substituted aralkyl group. $R^2$ and $R^3$ each represents a hydrogen atom, an optionally-substituted alkyl group, an optionally-substituted aryl group, an optionally-substituted monovalent heterocyclic ring residue, or an optionally-substituted aralkyl group. n represents an integer of 1 or 2. When n represents 2, two $R^2$ may be identical with or different from each other, and two $R^3$ may be identical with or different from each other).

25 Claims, 3 Drawing Sheets

U.S. PATENT DOCUMENTS

| | | |
|---|---|---|
| 4,572,884 A | 2/1986 | Sasaki |
| 4,859,556 A | 8/1989 | Sasaki |
| 4,892,949 A | 1/1990 | Sasaki |
| 5,246,808 A * | 9/1993 | Hanatani et al. ............ 549/435 |
| 5,486,441 A * | 1/1996 | Matsushima et al. .......... 430/74 |

FOREIGN PATENT DOCUMENTS

| | | |
|---|---|---|
| JP | 52-4188 | 2/1977 |
| JP | 54-150128 A | 11/1979 |
| JP | 54-151955 A | 11/1979 |
| JP | 55-52063 A | 4/1980 |
| JP | 58-32372 B2 | 7/1983 |
| JP | 58-198043 A | 11/1983 |
| JP | 59-95540 A | 6/1984 |
| JP | 59-97148 A | 6/1984 |
| JP | 59-191507 A | 10/1984 |
| JP | 63030853 A * | 2/1988 |
| JP | 01152461 A * | 6/1989 |
| JP | A 1-163748 | 6/1989 |
| JP | 2-154267 | 6/1990 |
| JP | 2-190862 A | 7/1990 |
| JP | 55-42380 B2 | 10/1990 |
| JP | 3-39306 B2 | 6/1991 |
| JP | 4-66023 B2 | 10/1992 |
| JP | 05281761 A * | 10/1993 |
| JP | 7-48324 A | 2/1995 |
| JP | 7-134430 | 5/1995 |
| JP | 09022130 A * | 1/1997 |
| JP | 9-319109 A | 12/1997 |
| JP | 11-305461 A | 11/1999 |
| JP | A 2000-075519 | 3/2000 |
| JP | 2001133995 A * | 5/2001 |
| JP | A 2001-133993 | 5/2001 |
| JP | A 2002-287388 | 10/2002 |
| JP | A 2003-202682 | 7/2003 |
| JP | A 2005-134652 | 5/2005 |

OTHER PUBLICATIONS

Diamond, Arthur S & David Weiss (eds.) Handbook of Imaging Materials, 2nd ed.. New York: Marcel-Dekker, Inc. (Nov. 2001) pp. 145-164.*

English language machine translation of JP 2001-133993 (2001).*

* cited by examiner

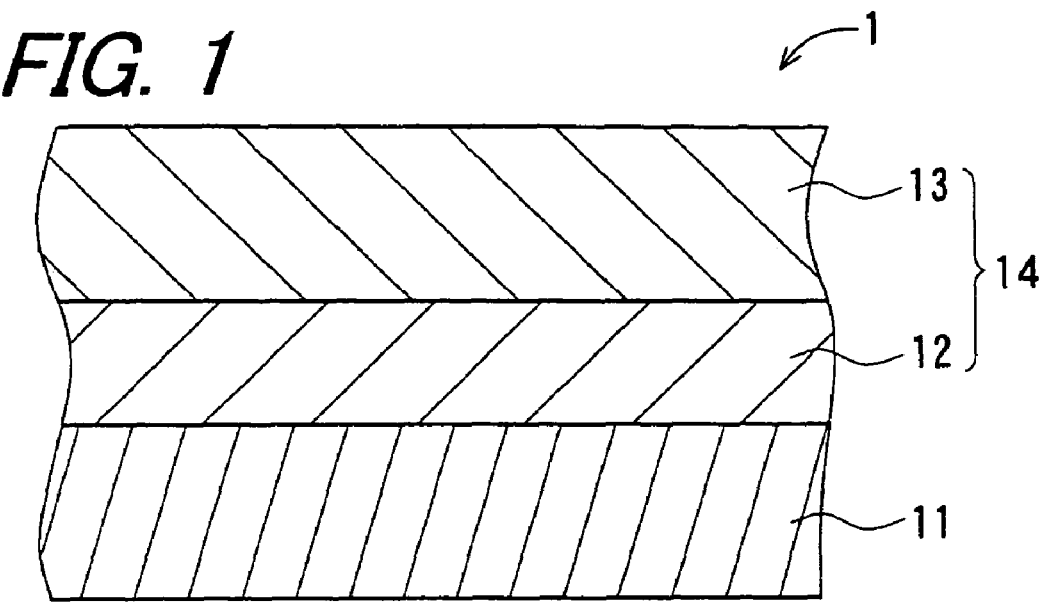
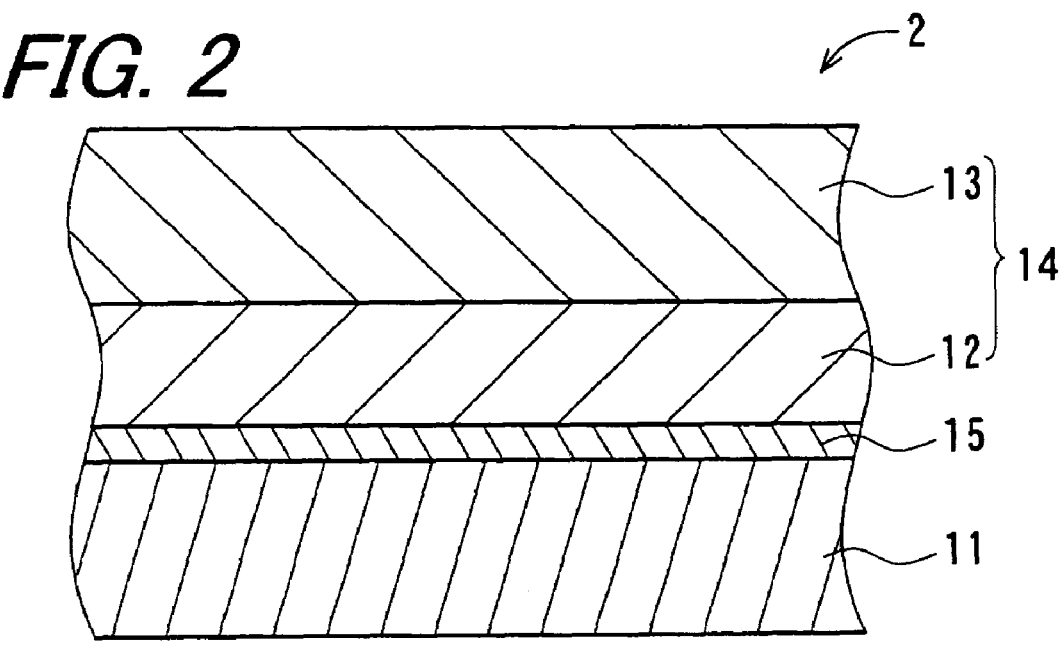

AMINE COMPOUND, MANUFACTURING METHOD THEREOF, ELECTROPHOTOGRAPHIC PHOTORECEPTOR USING AMINE COMPOUND AND IMAGE FORMING APPARATUS HAVING THE SAME

BACKGROUND OF THE INVENTION

1. Field of the Invention

The present invention relates to an amine compound and a manufacturing method thereof, as well as an electrophotographic photoreceptor using the amine compound and an image forming apparatus having the same.

2. Description of the Related Art

An electrophotographic image forming apparatus for forming images by using electrophotography (hereinafter referred to as an electrophotographic apparatus) has been used frequently such as for copying machines, printers or facsimile units. In the electrophotographic apparatus, images are formed byway of the following electrophotographic process. At first, a photosensitive layer of an electrophotographic photoreceptor equipped in the apparatus (hereinafter simply referred to as a photoreceptor) is uniformly charged to a predetermined potential by charging means such as a charging roller, applying exposure in accordance with image information by exposure means, thereby forming an electrostatic latent image on the photoreceptor. A developer is supplied to the formed electrostatic latent images and a toner as a component of the developer is adhered to the surface of the photoreceptor to develop the electrostatic latent image and visualize it as toner images. Thus formed toner image is transferred by transfer means from the surface of the photoreceptor onto a transfer material such as recording paper and fixed onto the transfer material by fixing means. Further, cleaning is applied to the photoreceptor after transfer of the toner image by cleaning means having a cleaning blade, etc. thereby eliminating the toner and the like remaining on the surface of the photoreceptor not transferred to the transfer material during transfer operation. Then, the surface of the photosensitive layer is charge-eliminated by a charge eliminator or the like to erase the electrostatic latent image.

In recent years, the electrophotography has been utilized not restricted only to the field of the image forming apparatus such as copying machines but utilized also in the field, for example, of printing plate materials, slide films or microfilms for which photography has been used so far, and it is also applied to high speed printers using lasers, Light Emitting Diode (abbreviated as LED) or Cathode Ray Tube (abbreviated as CRT) as a light source. Along with extension of the application range of the electrophotography, the demand for the electrophotographic photoreceptor has become higher and more versatile.

An electrophotographic photoreceptor is constituted by laminating a photosensitive layer containing a photoconductive material on a conductive support made of a conductive material. As the electrophotographic photoreceptor, an inorganic photoreceptor having a photosensitive layer mainly containing an inorganic photoconductive material such as selenium, zinc oxide or cadmium has been used generally. While the inorganic photoreceptor has basic properties as the photoreceptor to some extent, it involves a problem such that the formation of the film for the photosensitive layer is difficult and plasticity is poor, and the production cost is expensive. Further, since the inorganic photoconductive material generally has high toxicity and suffers from great restriction in view of production and handling.

As described above, since the inorganic photoconductive material and the inorganic photoreceptor using the same involve many drawbacks, research and development have been progressed for organic photoconductive materials. Since the organic photoreceptor using the organic photoconductive material has advantages such that the film formation property for the photosensitive material is favorable and the flexibility is excellent, as well as it is light in the weight, excellent in the transparency, and a photoreceptor showing good sensitivity to a wavelength region over a wide range can be designed easily by an appropriate sensitizing method. Thus, the organic photoreceptor has been under development as a predominant candidate for the electrophotographic photoreceptor. Further, the organic photoconductive material has been studied and developed generally in recent years and it has been utilized not only for the electrophotographic photoreceptor but also has been applied, for example, to electrostatic recording devices, sensor materials or organic Electro Luminescent (abbreviated as EL) devices.

While the organic photoreceptor has a drawback in view of the sensitivity and the durability in the early stage, such drawbacks have been improved remarkably by the development of a function separated electrophotographic photoreceptor in which charge-generating function and charge-transporting function are separately attained by different substances. Further, the function separated photoreceptor also has an advantage, in addition to the advantage of the organic photosensitive material described above, that the selection range for the material constituting the photosensitive layer is wide and an electrophotographic photoreceptor having optional characteristics can be manufactured relatively easily. The function separated photoreceptor includes a lamination type and a single layer type. The lamination type function separated photoreceptor is provided with a lamination type photosensitive layer in which a charge-generating layer containing a charge-generating substance for charge-generating function and a charge-transporting layer containing a charge-transporting substance for charge-transporting function are laminated. The charge-generating layer and the charge-transporting layer are formed usually in a state where the charge-generating substance and the charge-transporting substance are dispersed respectively in a binder resin as a binder. Further, the single layer type function separated photoreceptor is provided with a photosensitive layer of a single layer type in which both of the charge-generating substance and the charge-transporting substance are dispersed in a binder resin.

As the charge-generating substance used in the function separated photoreceptor, various substances such as phthalocyanine pigment, squilirium dye, azo pigment, perylene pigment, polynuclear quinone pigment, cyanine dye, squalic acid dye and pyrylium salt dye have been studied and various materials of high light fastness and high charge-generating ability have been proposed.

Further, various compounds have been proposed as the charge-transporting material, for example, pyrazoline compounds (for example, refer to Japanese Examined Patent publication JP-B 52-4188), hydrazone compounds (for example, refer to Japanese Unexamined Patent Publication JP-A 54-150128, Japanese Examined Patent Publication JP-B 55-42380, Japanese Unexamined Patent Publication JP-A 55-52063), triphenylamine compounds (for example, refer to Japanese Examined Patent Publication JP-B 58-32372, and Japanese Unexamined Patent Publications JP-A 2-190862 and JP-A 7-48324) and stylbene compounds (for example, Japanese Unexamined Patent Publications JP-A 54-151955 and JP-A 58-198043, Japanese Examined Patent Publications JP-B 3-39306 and JP-B 4-66023, Japanese Unexamined Patent Publications JP-A 59-95540, JP-A 59-97148, and JP-A 59-191057).

The charge-transporting substances must satisfy the following requirements:

(1) they are stable to light and heat,
(2) they are stable to active substances such as ozone, nitrogen oxide (chemical formula: $NO_x$) and nitric acid generated by corona discharging in discharging the photoreceptor,
(3) they have high charge-transporting ability,
(4) they have high compatibility with an organic solvent and a binder resin, and
(5) they can be manufactured easily and is inexpensive, etc.
However, while the charge-transporting substances disclosed, for example, in all of the patent documents described above can satisfy a portion of the demands but have not yet satisfy all of the demands at high level.

Further, in recent years, higher sensitivity has been demanded as the photoreceptor characteristics corresponding to the requirement of reduction in the size and high speed operation to electrophotographic apparatus such as digital copying machines and printers, and particularly high charge-transporting ability has been demanded for the charge-transporting substance. Further, in the high speed electrophotographic process, since the time from exposure to the development is short, a photoreceptor of excellent light responsiveness has been required. In a case where the light responsiveness of the photoreceptor is poor, that is, the decaying speed of the surface potential of the photosensitive layer by exposure is slow, since the residual potential rises and is used repetitively in a state where the surface potential is not decayed sufficiently. Therefore, the surface charges at a potion to be erased are not sufficiently erased by exposure to cause deterioration of the picture quality such as lowering of the image density in an early stage. In the function separated type photoreceptor, since the surface charges of the photosensitive layer at a portion irradiated with a light eliminated by the transportation of the charges generated from the charge-generating substance upon light absorption are transported by the charge-transporting substance to the surface of the photosensitive layer, the light responsiveness depends on the charge-transporting ability of the charge-transporting substance. Accordingly, high charge-transporting ability is required for the charge-transporting substance also with a view point of attaining a photoreceptor having high light responsiveness and capable of forming high quality images also in a high speed electrophotographic process.

Further, for attaining high durability of the electrophotographic apparatus, it is important that the electrophotographic photoreceptor has excellent durability to electric or mechanical external force and can operate stably for a long time. Then, in order to improve the mechanical durability of the photoreceptor, a high charge-transporting ability is required for the charge-transporting substance.

In a case where a photoreceptor is used being mounted on an electrophotographic apparatus, the surface layer of the photoreceptor is inevitably scraped at a portion thereof by a contact member such as a cleaning blade or a charge roller. In a case where the amount of film reduction on the surface layer of the photoreceptor is large, since the charge retainability of the photoreceptor is lowered failing to provide high quality images. Accordingly, for higher durability of the electrophotographic apparatus, it is demanded for a photoreceptor having a surface layer of high mechanical durability resistant to the contact member, that is, having a surface layer of high printing resistance with less amount of film reduction. In order to increase the printing resistance of the surface layer and improve the mechanical durability of the photoreceptor, it is generally necessary to increase the content of the binder resin in the charge-transporting layer used as the surface layer. However, in a case where the content of the binder resin is increased, since the content of the charge-transporting substance in the charge-transporting layer is relatively decreased, this brings about a problem that the charge-transporting ability of the charge-transporting layer is deteriorated and the light responsiveness is lowered. Since the light responsiveness of the photoreceptor depends on the charge-transporting ability of the charge-transporting substance as described above, a particularly high charge-transporting ability is demanded for the charge-transporting substance also for increasing the content of the binder resin thereby improving the mechanical durability of the photoreceptor, without lowering the light responsiveness.

However, the charge-transporting ability of the charge-transporting substances disclosed in all of the patent documents described above is not sufficient and a photoreceptor having sufficient light sensitivity and light responsiveness can not be attained even by the use of such charge-transporting substances. Particularly, sufficient sensitivity and light responsiveness cannot be obtained under a low temperature circumstance and images having an image density enough to practical use can not be formed.

Further, since the photoreceptor mounted on the electrophotographic apparatus is exposed to external light, for example, during maintenance, it is required for the photoreceptor that various characteristics as the photoreceptor are not deteriorated even when exposed to external light.

Further, in recent year, destruction of the global environment by chemical substances has bring about a problem and it has been keenly demanded for appropriately disposing liquid wastes, etc. formed in the course of manufacturing a photoreceptor and in the course of manufacturing materials constituting the photoreceptor. Particularly, since phosphoric reaction reagents used frequently in the course of producing stylbene compounds as disclosed described above, for example, phosphorous oxychloride reagent used in the Vilsmyer reaction for introducing formyl groups into aromatic compounds, heterocyclic compounds or olefins, and phosphorous reagent such as triphenyl phosphine or triethyl phosphate used in the Wittig reaction for converting carbonyl compounds into olefin give large burden to the global environments, disposal of the liquid wastes is troublesome in a case of using such reagents. Accordingly, it is demanded not to use solvents and reagents giving large burdens to the global environment as much as possible in the course of production of materials for the liquid sensitive body and the charge-transporting substances constituting the photoreceptor.

SUMMARY OF THE INVENTION

An object of the invention is to provide an amine compound having a high charge-transporting ability and capable of being prepared without using a phosphoric reaction reagent giving large burdens to the global environments, as well as a manufacturing method thereof.

Another object of the invention is to provide a highly reliable electrophotographic photoreceptor which is excellent in electric characteristics such as chargeability, sensitivity and light responsiveness, which does not lower favorable electric characteristics even when the surrounding circumstance such as temperature and humidify are changed and even when it is used repetitively or when it is exposed to external light and which is excellent in mechanical durability not causing deterioration of the picture quality in the formed images over a long time even in a case where it is used in a low temperature circumstance, or used for high speed electrophotographic process, as well as an image forming apparatus having the same.

The invention provides an amine compound represented by the following general formula (1).

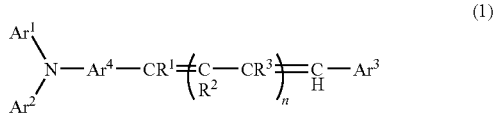

(in which $Ar^1$, $Ar^2$ and $Ar^3$ each represents an aryl group which may have a substituent, or a monovalent heterocyclic ring residue which may have a substituent. $Ar^4$ represents an arylene group which may have a substituent, or a bivalent heterocyclic ring residue which may have a substituent. $R^1$ represents an alkyl group which may have a substituent, an aryl group which may have a substituent, a monovalent heterocyclic ring residue which may have a substituent, or an aralkyl group which may have a substituent. $R^2$ and $R^3$ each represents a hydrogen atom, an alkyl group which may have a substituent, an aryl group which may have a substituent, a monovalent heterocyclic ring residue which may have a substituent, or an aralkyl group which may have a substituent. n represents an integer of 1 or 2. When n represents 2, two $R^2$ may be identical with or different from each other, and two $R^3$ may be identical with or different from each other).

Further, in the invention, the amine-compound is an amine-butadiene compound represented by the general formula (2).

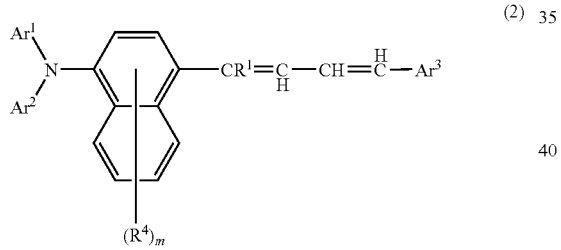

(in which $R^4$ represents an alkyl group which may have a substituent, an alkoxy group which may have a substituent, a dialkylamino group represented by $—NR^5R^6$ ($R^5$ and $R^6$ each represents an alkyl group which may have a substituent), an aryl group which may have a substituent, a halogen atom or a hydrogen atom. m represents an integer of from 1 to 6. When m is 2 or more, a plurality of $R^4$ maybe identical with or different from each other, and may bond with each other to form a ring structure. $Ar^1$, $Ar^2$, $Ar^3$ and $R^1$ have the same meanings as those in the general formula (1)).

Further, the invention provides an electrophotographic photoreceptor comprising:
  a conductive support made of a conductive material; and
  a photosensitive layer provided on the conductive support and containing a charge-generating substance and a charge-transporting substance,
  wherein the charge-transporting substance contains the amine compound described above.

Further, in the invention, the charge-generating substance contains an oxotitanium phthalocyanine compound.

Further, in the invention, the oxotitanium phthalocyanine compound is an oxotitanium phthalocyanine compound having a crystal structure showing a distinct diffraction peak at least at a Bragg angle 2θ (error: 2θ±0.2°) of 27.2° in an X-rays diffraction spectrum relative to Cu—Kα characteristic X-ray (wavelength : 1.54 Å).

Further, in the invention, the photosensitive layer comprises a lamination of a charge-generating layer containing the charge-generating substance and a charge-transporting layer containing the charge-transporting substance.

Further, in the invention, the charge-transporting layer further contains a binder resin, and the ratio A/B between weight A for the amine compound represented by the general formula (1) and weight B for the binder resin in the charge-transporting layer is 10/30 or more and 10/12 or less.

Further, in the invention, an intermediate layer is further present between the conductive support and the photosensitive layer.

Further, the invention provides an image forming apparatus comprising:
  the electrophotographic photoreceptor described above;
  charging means for charging the electrophotographic photoreceptor;
  exposure means for applying exposure to the charged electrophotographic photoreceptor; and
  developing means for developing an electrostatic latent image formed by exposure.

Further, the invention provides a method of preparing the amine compound described above comprising a step of:
  reacting an amine compound represented by the general formula (3)

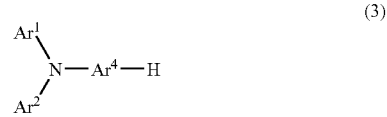

(wherein $Ar^1$, $Ar^2$ and $Ar^4$ have the same meanings as those in the general formula (1)), and
an acyl halide represented by the following general formula (4-1):

(wherein X represents a halogen atom, and $R^1$ have the same meanings as those in the general formula (1)), or
a carboxylic acid anhydride represented by the following general formula (4-2):

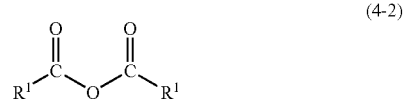

(wherein $R^1$ have the same meanings as those in the general formula (1)) under the presence of Lewis acid, to synthesize an amine-carbonyl intermediate product represented by the general formula (5):

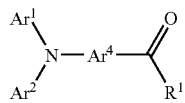

(wherein $Ar^1$, $Ar^2$, $Ar^4$ and $R^1$ have the same meanings as those in the general formula (1)), and a step of reacting the obtained amine-carbonyl intermediate product represented by the general formula (5) with a Grignard reagent prepared by reacting an allyl halide represented by the following general formula (6-1):

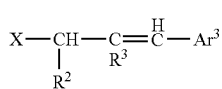

(wherein X represents a halogen atom, $Ar^3$, $R^2$ and $R^3$ have the same meanings as those in the general formula (1)) or the following general formula (6-2):

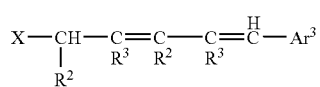

(wherein X represents a halogen atom, $Ar^3$, $R^2$ and $R^3$ have the same meanings as those in the general formula (1)) and metallic magnesium.

According to the invention, the amine compound represented by the general formula (1), particularly, the amine-butadiene compound represented by the general formula (2) has high charge-transporting ability. Accordingly, by incorporating the amine compound represented by the general formula (1), preferably, the amine-butadiene compound represented by the general formula (2) as the charge-transporting substance in the photosensitive layer of the electrophotographic photoreceptor, a highly reliable electrophotographic photoreceptor excellent in electric characteristics such as chargeability, sensitivity and light responsiveness and with no deterioration of good electric characteristics even when surrounding circumstances such as temperature and humidity are changed, even when it is used repetitively or even when it is exposed to external light can be attained. Further, a device of excellent responsiveness can be provided by using the amine compound represented by the general formula (1), preferably, the amine-butadiene compound represented by the general formula (2) to a sensor material, El device or electrostatic recording device.

Further, since the photosensitive layer can be provided with excellent wear resistant property to improve the printing resistance of the photosensitive layer by incorporating the amine compound represented by the general formula (1) to the photosensitive layer of the electrophotographic photoreceptor, an electrophotographic photoreceptor of excellent mechanical durability can be attained. It is considered that the photosensitive layer can be provided with excellent wear resistant property by incorporating the amine compound represented by the general formula (1), because the mechanical strength of the amine compound per se represented by the general formula (1) is high. That is, since the substitution pattern at the end of multiple bond of the amine compound represented by the general formula (1) is 1-substitution (=CH—$Ar^3$), a stacking structure of an ideal stacked state in which molecules are packed densely can be attained. Accordingly, it is considered that the mechanical strength of the amine compound represented by the general formula (1) is high and the photosensitive layer is provided with excellent wear resistant property by incorporating the amine compound represented by the general formula (1) in the photosensitive layer.

As described above, a highly reliable electrophotographic photoreceptor excellent in the electric characteristic, circumstantial stability, and electrical and mechanical durability can be attained by incorporating the amine compound represented by the general formula (1), preferably, the amine-butadiene compound represented by the general formula (2) in the photosensitive layer. By the use of the electrophotographic photoreceptor described above, high quality images can be formed even under a low temperature circumstance or in a high speed electrophotographic process for a long time with no deterioration of the picture quality.

Further, the amine compound represented by the general formula (1) can be prepared by synthesizing an amine-carbonyl intermediate product represented by the general formula (5) through the Friedel-craft acylating reaction by using the amine compound represented by the general formula (3) and the halogenated acyl represented by the general formula (4-1) or the carboxylic acid anhydride represented by the general formula (4-2) and then conducting Grignard reaction between the obtained amine carbonyl intermediate product represented by the general formula (5) and a Grignard reagent prepared from an allyl halide represented by the general formula (6-1) or the general formula (6-2), and metallic magnesium.

As described above, the amine compound represented by the general formula (1) can be prepared without using a phosphoric reaction reagent giving large burdens on the global environment. Therefore, liquid wastes formed in the course of preparing the amine compound represented by the general formula (1) give less burdens on the global environment, can be disposed easily, with less expense necessary for the disposal of the liquid wastes. Accordingly, the production cost for the amine compound represented by the formula (1) is low. Further, among the amine compounds represented by the general formula (1), since the amine-butadiene compound represented by the general formula (2) has a naphthaleneamine-end-substituted butadiene structure which can be synthesized most easily, the production cost is further lower. Accordingly, by using the amine compound represented by the general formula (1), preferably, the amine-butadiene compound represented by the general formula (2) as the charge-transporting substance, a highly reliable electrophotographic photoreceptor excellent in the electric characteristics, the circumstantial stability, and electrical and mechanical durability as described above can be produced at a low product cost.

Further, according to the invention, the amine compound represented by the general formula (1), preferably, the amine-butadiene compound represented by the general formula (2) is contained as the charge-transporting substance in the photosensitive layer of the electrophotographic photoreceptor. Accordingly, it is possible to obtain a highly reliable electrophotographic photoreceptor excellent in the electric characteristics such as chargeability, sensitivity and light responsiveness, not suffering from deterioration of good electric characteristics even when surrounding circumstances such as temperature and humidity are changed and even when it is used repetitively or exposed to external light, and which is excellent in mechanical durability and causing no deterioration of picture quality for the formed images for a long time even which it is used under low temperature circumstance and used for the high speed electrophotographic process.

Further, according to the invention, the photosensitive layer of the electrophotographic photoreceptor is incorporated, as a charge-generating substance, with an oxotitanium phthalocyanine compound, preferably, an oxotitanium phthalocyanine compound having a crystal structure showing a distinct diffraction peak at least at a Bragg angle $2\theta$ (error: $2\theta \pm 0.2°$) of 27.2° in an X-ray diffraction spectrum relative to Cu—K$\alpha$ characteristic X-rays (wavelength: 1.54 Å). Since the oxotitanium phthalocyanine compound is a charge-generating substance having a high charge-generating efficiency and charge injection efficiency, it generates a great amount of charges upon absorption of light and injects the generated charges efficiently to the charge-transporting substance without storing them in the inside. Since the photosensitive layer is incorporated with the amine compound represented by the general formula (1) of high charge-transporting ability as the charge-transporting substance, charges generated in the oxotitanium phthalocyanine compound by light absorption are efficiently injected to the amine compound represented by the general formula (1) and transported smoothly to the surface of the photosensitive layer. Accordingly, an electrophotographic photoreceptor of high sensitivity and high resolution can be obtained by incorporating the oxotitanium phthalocyanine compound, preferably, the oxodititanium phthalocyanine compound having the specified crystal structure as described above in the photosensitive layer together with the amine compound represented by general formula (1).

Further, according to the invention, the photosensitive layer of the electrophotographic photoreceptor is constituted by laminating the charge-generating layer containing the charge-generating substance and the charge-transporting layer containing the charge-transporting substance containing the amine compound represented by the general formula (1). Thus, materials optimal to the charge-generating function and the charge-transporting function can be selected respectively as the material for constituting each of the layers by sharing the charge-generating function and the charge-transporting function to separate layers. Therefore, an electrophotographic photoreceptor particularly excellent in the electric characteristics such as chargeability, sensitivity and light responsiveness and having particularly high durability with increased stability during repetitive use can be obtained.

Further, according to the invention, the ratio A/B between the weight A for the amine compound represented by the general formula (1) and the weight B for the binder resin in the charge-transporting layer is 10/30 or more and 10/12 or less. Since this can improve the printing resistance of the charge-transporting layer, the mechanical durability of the electrophotographic photoreceptor can be improved further by the synergistic effect with the excellent wear resistant property of the charge-transporting layer provided by the incorporation of the amine compound represented by the general formula (1). Further, since the amine compound represented by the general formula (1) has a high charge-transporting ability, even when the ratio of the binder resin in the charge-transporting layer is increased by defining the ratio A/B to 10/12 or less as described above, the electrophotographic photoreceptor shows a sufficiently high light responsiveness. That is, since the ratio A/B can be set to 10/30 or more and 10/12 or less without lowering the light responsiveness, an electrophotographic photoreceptor having high light responsiveness particularly excellent in the mechanical durability can be obtained.

Further, according to the invention, an intermediate layer is provided between the conductive support and the photosensitive layer. Since this can prevent injection of charges from the conductive support to the photosensitive layer, deterioration of the chargeability of the photosensitive layer can be prevented, and decrease of the surface charges at a portion other than the exposed portion can be suppressed to prevent occurrence of defects such as fogging to the images. Further, since the defects on the surface of the conductive support can be covered to obtain a uniform surface, the film forming property of the photosensitive layer can be improved. Further, since the intermediate layer functions as an adhesive between the conductive support and the photosensitive layer, peeling of the photosensitive layer from the conductive support can be suppressed.

Further, according to the invention, since the electrophotographic photoreceptor provided to the image forming apparatus is excellent in the electric characteristics such as chargeability, sensitivity and light responsiveness, not suffering from lowering of good electric characteristics even when the surrounding circumstances such as temperature and humidity are changed or even when it is used repetitively and is also excellent in the mechanical durability, an image forming apparatus of high reliability capable of forming images stably with no deterioration of picture quality in various circumstances over a long time can be obtained. Further, since the electrophotographic photoreceptor provided to the image forming apparatus suffers from no deterioration of the picture quality to the formed images, it is possible to attain an image forming apparatus capable of forming images at high quality at high speed. Further, since the electric characteristic of the electrophotographic photoreceptor provided to the image forming apparatus is not deteriorated even when exposed to the external light, it is possible to suppress degradation of the picture quality caused by the exposure of the electrophotographic photoreceptor to the external light, for example, during maintenance.

BRIEF DESCRIPTION OF THE DRAWINGS

Other and further objects, features, and advantages of the invention will be more explicit from the following detailed description taken with reference to the drawings wherein:

FIG. 1 is a fragmentary cross sectional view schematically showing the constitution of an electrophotographic photoreceptor according to a first embodiment of the invention;

FIG. 2 is a fragmentary cross sectional view schematically showing the constitution of an electrophotographic photoreceptor according to a second embodiment of the invention;

DETAILED DESCRIPTION OF THE PREFERRED EMBODIMENTS

Figure 3:
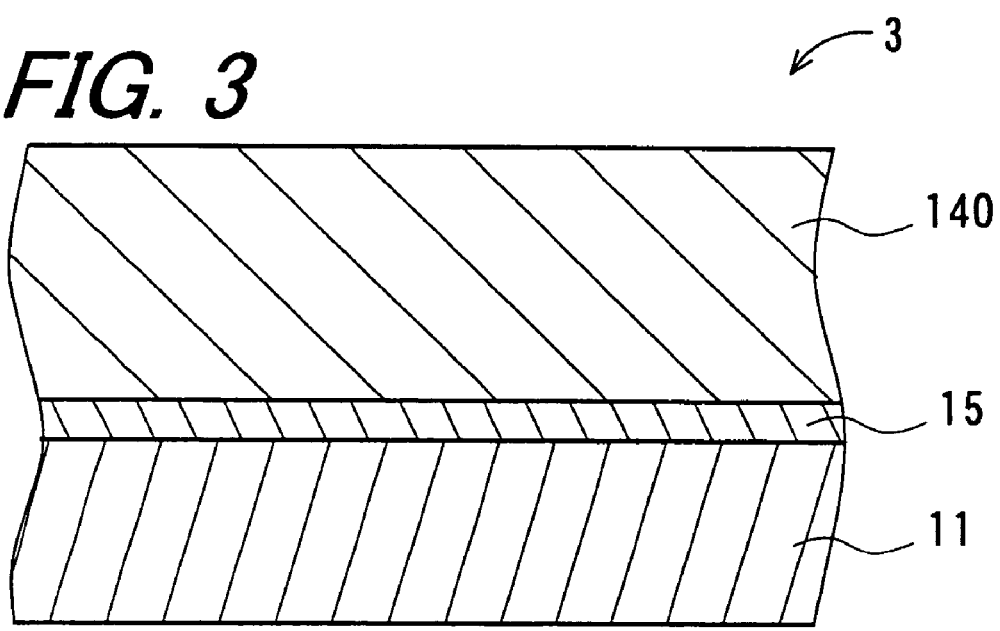
FIG. 3 is a fragmentary cross sectional view schematically showing the constitution of an electrophotographic photoreceptor according to a third embodiment of the invention.

Now referring to the drawings, preferred embodiments of the invention are described below.

The amine compound of the invention is represented by the following general formula (1):

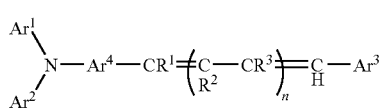

(1)

In the general formula (1), $Ar^1$, $Ar^2$ and $Ar^3$ each represents a aryl group which may have a substituent, or a monovalent heterocyclic ring residue which may have a substituent. $Ar^4$ represents an arylene group which may have a substituent, or a bivalent heterocyclic ring residue which may have a substituent. $R^1$ represents an alkyl group which may have a substituent, an aryl group which may have a substituent, a monovalent heterocyclic ring residue which may have a substituent, or an aralkyl group which may have a substituent. $R^2$ and $R^3$ each represents a hydrogen atom, an alkyl group which may have a substituent, an aryl group which may have a substituent, a monovalent heterocyclic ring residue which may have a substituent, or an aralkyl group which may have a substituent. n represents an integer of 1 or 2. When n represents 2, two $R^2$ may be identical with or different from each other, and two $R^3$ may be identical with or different from each other.

Among the amine compounds represented by the general formula (1), preferred examples can include amine-butadiene compounds represented by the following general formula (2):

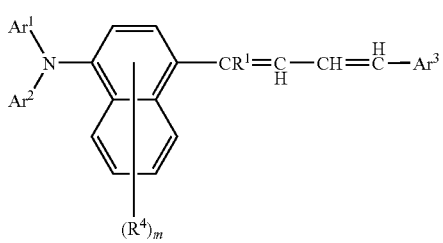

(2)

In the general formula (2), $R^4$ represents an alkyl group which may have a substituent, an alkoxy group which may have a substituent, a dialkyl amino group represented by $-NR^5R^6$ ($R^5$ and $R^6$ each represents an alkyl group which may have a substituent), an aryl group which may have a substituent, a halogen atom or a hydrogen atom. m represents an integer of from 1 to 6. When m is 2 or more, a plurality of $R^4$ maybe identical with or different from each other, and may bond with each other to form a ring structure. $Ar^1$, $Ar^2$, $Ar^3$ and $R^1$ have the same meanings as those in the general formula (1).

The amine compound represented by the general formula (1), particularly, the amine-butadiene compound represented by the general formula (2) has high charge-transporting ability. Accordingly, by incorporating the amine compound represented by the general formula (1), preferably, the amine-butadiene compound represented by the general formula (2) as the charge-transporting substance in the photosensitive layer of the electrophotographic photoreceptor, a highly reliable electrophotographic photoreceptor excellent in electric characteristics such as chargeability, sensitivity and light responsiveness and with no deterioration of good electric characteristics even when surrounding circumstances such as temperature and humidity are changed, even when it is used repetitively or even when it is exposed to external light can be attained. Further, a device of excellent responsiveness can be provided by using the amine compound represented by the general formula (1), preferably, the amine-butadiene compound represented by the general formula (2) to a sensor material, El device or electrostatic recording device.

Further, since the photosensitive layer can be provided with excellent wear resistant property to improve the printing resistance of the photosensitive layer by incorporating the amine compound represented by the general formula (1) to the photosensitive layer of the electrophotographic photoreceptor, an electrophotographic photoreceptor of excellent mechanical durability can be attained. It is considered that the photosensitive material can be provided with excellent wear resistant property by incorporating the amine compound represented by the general formula (1), because the mechanical strength of the amine compound per se represented by the general formula (1) is high. That is, since the substitution pattern at the end of multiple bond of the amine compound represented by the general formula (1) is 1-substitution ($=CH-Ar^3$), a stacking structure of an ideal stacked state in which molecules are packed densely can be attained. Accordingly, it is considered that the mechanical strength of the amine compound represented by the general formula (1) is high and the photosensitive layer is provided with excellent wear resistant property by incorporating the amine compound represented by the general formula (1) in the photosensitive layer.

As described above, a highly reliable electrophotographic photoreceptor excellent in the electric characteristic, circumstantial stability, and electrical and mechanical durability can be attained by incorporating the amine compound represented by the general formula (1), preferably, the amine-butadiene compound represented by the general formula (2) in the photosensitive layer. By the use of the electrophotographic photoreceptor described above, high quality images can be formed even under a low temperature circumstance or in a high speed electrophotographic process for a long time with no deterioration of the picture quality.

Further, the amine compound represented by the general formula (1) can be prepared without using a phosphoric reaction reagent giving large burdens on the global environment. Therefore, liquid wastes formed in the course of preparing the amine compound represented by the general formula (1) gives less burdens on the global environment, can be disposed easily, with less expense necessary for the disposal of the liquid wastes. Accordingly, the production cost for the amine compound represented by the formula (1) is low. Further, among the amine compounds represented by the general formula (1), since the amine-butadiene compound represented by the general formula (2) has a naphthalene amine-end-substituted butadiene structure which can be synthesized most easily, the production cost is further lower. Accordingly, by using the amine compound represented by the general formula (1), preferably, the amine-butadiene compound represented by the general formula (2) as the charge-transporting substance, a highly reliable electrophotographic photoreceptor excellent in the electric characteristics, the circumstantial stability, and electrical and mechanical durability as described above can be produced at a low product cost.

In the specification of the invention, the aryl group can include, for example, phenyl, naphthyl, biphenylyl, terphenyl, pyrenyl and anthryl. A substituent which can be present on the aryl group can include, for example, an alkyl group such as methyl, ethyl and propyl, haloalkyl group such as trifluoromethyl, alkenyl group such as 2-propenyl and styryl, alkoxy group such as methoxy, ethoxy and propoxy, alkylamino group such as methylamino and ethylamino, dialkyl amino group such as dimethylamino, diethylamino, and diisopropylamino, halogen atom such as fluorine atom, chlorine atom and bromine atom, aryloxy group such as phenoxyl group or arylthio groups such as phenylthio. The aryl group having the substituent can include, for example, tollyl, methoxyphenyl, phenoxyphenyl, p-(phenolthio)phenyl, and p-styryl phenyl.

The monovalent heterocyclic ring residue can include, for example, a five- or six-membered or condensed ring, preferably, a five-membered heterocyclic ring group having an oxygen atom, nitrogen atom, sulfur atom, selenium atom or tellurium atom, preferably, an oxygen atom, nitrogen atom or sulfur atom as a hetero atom, such as furil, thienyl, thiazoryl, benzofuril, benzothiophenyl, benzothiazoryl, benzooxazolyl and benzoylpyranyl. A substituent which can be present on the monovalent heterocyclic ring residue can include those similar to substituents which can be present on the aryl group. A monovalent heterocyclic ring residue having the substituent can include, for example, N-methylindolyl and N-ethylcarbozolyl.

The arylene group can include, for example, p-phenylene, 1,4-naphtylene, pyrenylene and 4,4'-biphenylylene. A substituent which can be present on the arylene group can include those similar to the substituents which can be present on the aryl group. An arylene group having the substituent can include, for example, 2-methyl-1,4-phenylene and 2-methoxy-1,4-phenylene.

The bivalent heterocyclic ring residue can include, for example, a five- or six-membered or condensed ring, preferably, a five-membered heterocyclic ring group having an oxygen atom, nitrogen atom, sulfur atom, selenium atom or tellurium atom, preferably an oxygen atom, nitrogen atom or sulfur atom as a hetero atom, such as 1,4-furilene, 1,4-thienylene, 1,4-thiazolylene and 4,5-carbozolylene. A substituent which can be present on the bivalent heterocyclic ring residue can include those similar to the substituents which can be present on the aryl group. A bivalent heterocyclic ring residue having the substituent can include, for example, N-ethyl-4,5-carbazolylene.

The alkyl group is preferably an alkyl group having from 1 to 6 carbon atoms and can include, for example, chained alkyl groups such as of methyl, ethyl, n-propyl, isopropyl and t-butyl, and cycloalkyl groups such as cyclohexyl and cyclopentyl. A substituent which can be present on the alkyl group can include those similar to substituents which can be present on the aryl group. The alkyl group having a substituent can include, for example, a haloalkyl group such as trifluoromethyl, fluoromethyl and 2,2,2-trifluoroethyl, alkoxyalkyl group such as 1-methoxyethyl and methoxymethyl and alkyl group substituted with a monovalent heterocyclic ring residue such as 2-thienylmethyl.

The aralkyl group can include, for example, benzyl and 1-naphthylmethyl. The substituent which can be present on the aralkyl group can include those similar to the substituent which can be present on the aryl group. The aralkyl group having the substituent can include, for example, p-methoxybenzyl.

The alkoxy group is preferably an alkoxy group having from 1 to 4 carbon atoms, and can include, for example, methoxy, ethoxy, n-propoxy and isopropoxy. A substituent which can be present on the alkoxy group can include those similar to the substituent which can be present on the aryl group.

The dialkylamino group represented by —NR$^5$R$^6$ can include, for example, dimethylamino, diethylamino and diisopropylamino. Among them, those in which R$^5$ and R$^6$ each represents an alkyl group having from 1 to 4 carbon atoms are preferred.

The halogen atom can include, for example, a fluorine atom and a chlorine atom.

Among the amine compounds represented by the general formula (1), compounds especially excellent in view of the characteristics, cost and productivity are those in which Ar$^1$ and Ar$^2$ each represents p-tollyl or p-methoxyphenyl, Ar$^3$ represents phenyl, p-tollyl, p-methoxyphenyl, α-naphthyl, 1-furil, 2-benzofuril or 1-thienyl, Ar$^4$ represents p-phenylene, 2-methyl-1,4-phenylene, 2-methoxy-1,4-phenylene, 4,4'-biphenlylene or 1,4-naphtylene, R$^1$ represents methyl, R$^2$ and R$^3$ each represents a hydrogen atom and n represents 1.

Specific examples of the amine compound of the invention represented by the general formula (1) can include Exemplified Compounds No. 1 to No. 40 shown in Tables 1 to 4 described below, however, the amine compound of the invention is not restricted to them. In the Tables 1 to 4, each of the exemplified compounds is represented by a group corresponding to each group of the general formula (1). For example, the exemplified compounds No. 1 shown in Table 1 is an amine compound represented by the following structural formula (1-1).

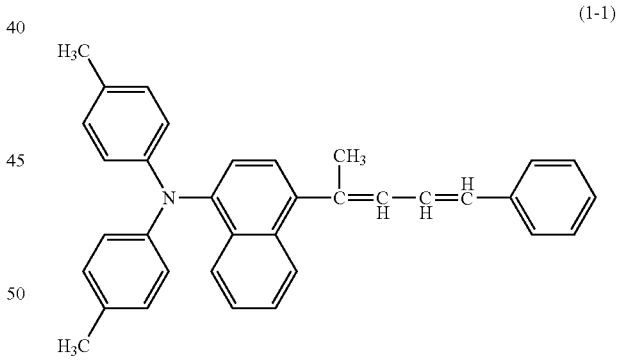

(1-1)

TABLE 1

| Compound No. | Ar$^1$ | Ar$^2$ | R$^1$ | Ar$^3$ | Ar$^4$ | n | =CR$^2$—CR$^3$= |
|---|---|---|---|---|---|---|---|
| 1 | H$_3$C—⌬— | H$_3$C—⌬— | —CH$_3$ | ⌬ | naphthyl | 1 | =CH—CH= |

TABLE 1-continued
| Compound No. | Ar¹ | Ar² | R¹ | Ar³ | Ar⁴ | n | =CR²—CR³= |
|---|---|---|---|---|---|---|---|
| 2 |  |  | —CH₃ | 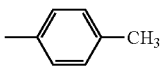 | 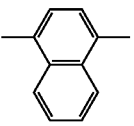 | 1 | =CH—CH= |
| 3 |  |  | —CH₃ | 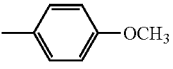 | 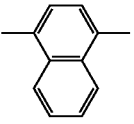 | 1 | =CH—CH= |
| 4 |  |  | —CH₃ | 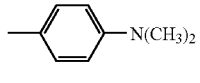 | 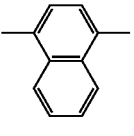 | 1 | =CH—CH= |
| 5 |  |  | —CH₃ | 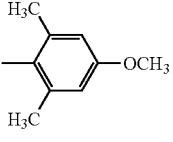 | 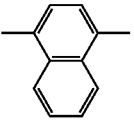 | 1 | =CH—CH= |
| 6 |  |  | —CH₃ | 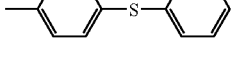 | 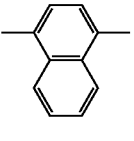 | 1 | =CH—CH= |
| 7 |  |  | —CH₃ | 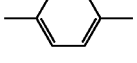 | 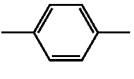 | 1 | =CH—CH= |
| 8 |  |  | —CH₃ | 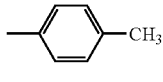 | 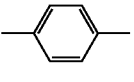 | 2 | =(CH—CH)₂= |
| 9 |  |  | —CH₃ | 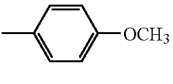 | 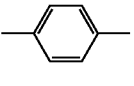 | 1 | =CH—CH= |
| 10 |  |  | —CH₃ | 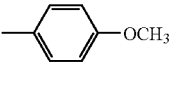 | 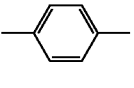 | 1 | =CH—CH= |
| 11 |  |  | —CH₃ | 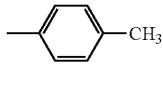 | 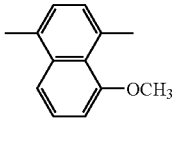 | 1 | =CH—CH= |
| 12 |  |  | —CH₃ | 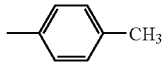 | 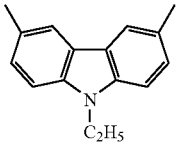 | 1 | =CH—CH= |

TABLE 2
| Compound No. | Ar¹ | Ar² | R¹ | Ar³ | Ar⁴ | n | =CR²—CR³= |
|---|---|---|---|---|---|---|---|
| 13 | 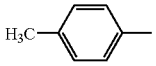 | 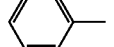 | —CH₃ |  |  | 1 | =CH—CH= |
| 14 | 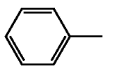 | 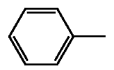 | —CH₃ | 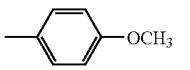 |  | 1 | =CH—CH= |
| 15 | 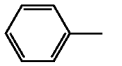 | 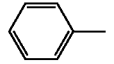 | —CH₃ | 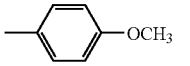 |  | 2 | 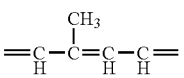 |
| 16 | 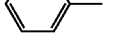 | 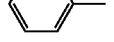 | —CH₃ | 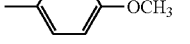 | 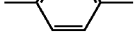 | 2 | 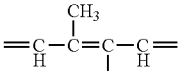 |
| 17 | 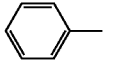 | 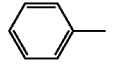 | —CH₃ | 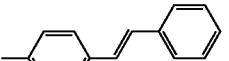 |  | 1 | =CH—CH= |
| 18 | 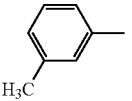 |  | —CH₃ | 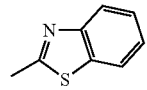 |  | 1 | =CH—CH= |
| 19 | 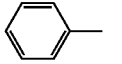 | 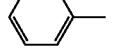 | 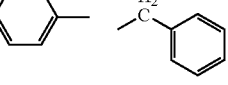 | 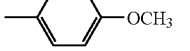 |  | 1 | =CH—CH= |
| 20 | 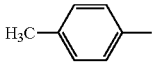 | 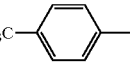 | —CH₃ | 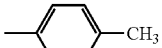 | 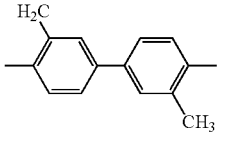 | 1 | =CH—CH= |
| 21 | 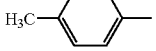 | 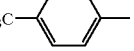 | —CH₃ | 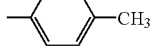 | 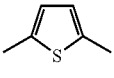 | 1 | =CH—CH= |
| 22 | 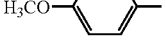 | 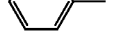 | —CH₃ | 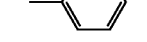 |  | 1 | =CH—CH= |
| 23 | 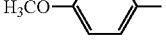 | 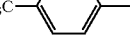 | —CH₃ | 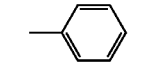 |  | 1 | =CH—CH= |
| 24 | 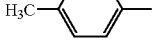 | 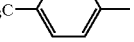 | —CH₃ | 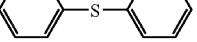 | 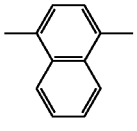 | 1 | =CH—CH= |
TABLE 3
| Compound No. | Ar¹ | Ar² | R¹ | Ar³ | Ar⁴ | n | =CR²—CR³= |
|---|---|---|---|---|---|---|---|
| 25 | 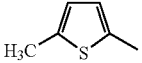 | 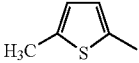 | —CH₃ | 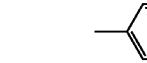 | 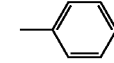 | 1 | =CH—CH= |

TABLE 3-continued

| Compound No. | Ar¹ | Ar² | R¹ | Ar³ | Ar⁴ | n | =CR²—CR³= |
|---|---|---|---|---|---|---|---|
| 26 | H₃CO—⟨⟩— | H₃C—⟨⟩— | —CH₃ | ⟨⟩— | naphthyl | 1 | =CH—CH= |
| 27 | H₃C—⟨⟩— | H₃C—⟨⟩— | —CH₂CF₃ | ⟨⟩— | naphthyl | 1 | =CH—CH= |
| 28 | H₃C—⟨⟩— | H₃C—⟨⟩— | —CH₃ | furyl | ⟨⟩— | 1 | =CH—CH= |
| 29 | H₃C—⟨⟩— | H₃C—⟨⟩— | —CH₃ | ⟨⟩— | naphthyl | 2 | =CH—C(CH₃)=CH—CH= |
| 30 | H₃C—⟨⟩— | H₃C—⟨⟩— | —CH₃ | ⟨⟩— | naphthyl | 2 | ={CH—CH=}₂ |
| 31 | H₃C—⟨⟩— | H₃C—⟨⟩— | —CH₃ | chroman | naphthyl | 2 | ={CH—CH=}₂ |
| 32 | H₃C—⟨⟩— | H₃C—⟨⟩— | —CH₃ | —⟨⟩—S—⟨⟩— | naphthyl | 2 | ={CH—CH=}₂ |
| 33 | ⟨⟩— | ⟨⟩— | —C₂H₅ | —⟨⟩—OCH₃ | ⟨⟩— | 2 | ={CH—CH=}₂ |
| 34 | ⟨⟩— | ⟨⟩— | —CH₂—⟨⟩ | ⟨⟩— | naphthyl | 2 | ={CH—CH=}₂ |
| 35 | ⟨⟩— | ⟨⟩— | —C₂H₅ | ⟨⟩— | ⟨⟩— | 2 | ={CH—CH=}₂ |
| 36 | H₃C—⟨⟩— | H₃C—⟨⟩— | —CH₃ | —⟨⟩—OCH₃ | naphthyl | 2 | ={CH—CH=}₂ |

TABLE 4

| Compound No. | Ar¹ | Ar² | R¹ | Ar³ | Ar⁴ | n | =CR²—CR³= |
|---|---|---|---|---|---|---|---|
| 37 | ⟨⟩— | ⟨⟩— | —nC₃H₇ | —⟨⟩—OCH₃ | ⟨⟩— | 2 | ={CH—CH=}₂ |

TABLE 4-continued

| Compound No. | Ar¹ | Ar² | R¹ | Ar³ | Ar⁴ | n | =CR²—CR³= |
|---|---|---|---|---|---|---|---|
| 38 | H₃C-⌬- | ⌬- | -⌬ | ⌬- | ⌬- | 2 | =(CH—CH)₂= |
| 39 | H₃C-⌬- | naphthyl | -⌬-CH₃ | ⌬- | anthracenyl | 2 | =(CH—CH)₂= |
| 40 | H₃CO-⌬- | ⌬- | thienyl-CH₃ | ⌬- | ⌬- | 2 | =(CH—CH)₂= |

Next, a process for producing the amine compound of the invention represented by the general formula (1) is to be explained. The amine compound of the invention represented by the general formula (1) can be produced by various methods. However, upon introduction of a carbonyl group which is necessary for extension of carbon chains, when an aldehyde group is introduced by Vilsmyer reaction which has been used frequently, so far phosphorus oxychloride as a phosphoric reaction reagent has to be used. Further, when a carbonyl compound obtained by the introduction of a carbonyl group is intended to be converted into an olefin by Wittig reaction, a triphenyl phosphine or triethyl phosphite as a phosphoric reaction reagent has to be used. Then, in the production process for the amine compound according to the invention, Friedel-craft acylating reaction using no phosphoric reaction reagent is used upon introduction of a carbonyl group which is necessary for the extension of carbon chains, and Grignard reaction using no phosphoric reaction reagent is used also upon olefination of a carbonyl compound. Specifically, the amine compound represented by the general formula (1) is produced as follows.

At first, the amine compound represented by the following general formula (3) is acylated by Friedel-craft acylating reaction. Specifically, an amine compound represented by the following general formula (3) and an acyl halide represented by the following general formula (4-1) or a carboxylic acid anhydride represented by the general formula (4-2) are reacted in the presence of a Lewis acid to produce an amine-carbonyl intermediate represented by the following general formula (5).

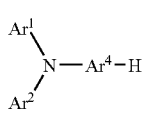

(wherein Ar¹, Ar² and Ar⁴ have the same meanings as those in the general formula (1)).

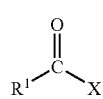

(wherein X represents a halogen atom, and R¹ has the same meanings as those in the general formula (1)).

(wherein R¹ has the same meanings as those in the general formula (1)).

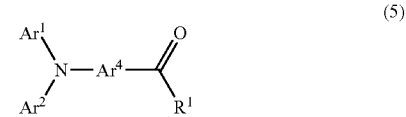

(wherein Ar¹, Ar², Ar⁴ and R¹ have the same meanings as those in the general formula (1)).

The Friedel-craft acylating reaction is conducted, for example, as follows. A Lewis acid is added in an appropriate solvent, an acyl halide represented by the general formula (4-1) or a carboxylic acid anhydride represented by the general formula (4-2) is added thereto under cooling, stirred for about from 0.5 to 1 hour to prepare a Friedel-craft acylating reagent. A solvent to be used can include, for example, halogenated hydrocarbons such as 1,2-dichloroethane, dichloromethane, etc. and aromatic hydrocarbons such as nitrobenzene, etc. The Lewis acid can include, for example, aluminum chloride, tin chloride, etc. and zinc chloride. The Lewis acid is used in an amount of from 1.0 to 1.2 mol equivalent relative to the acyl halide represented by the general formula (4-1) and in an amount of from 2.0 to 2.2 mol equivalent relative to the carboxylic acid anhydride represented by the general formula (4-2).

The amine compound represented by the general formula (3) is added under cooling to the solution in which the Friedel-craft acylating reagent is thus prepared, stirred for 2 to 8 hours at a temperature of −40° C. to 30° C. After completing the reaction, the reaction solution was optionally stood to cool and subjected to hydrolysis with a 1 to 8N aqueous alkaline solution under cooling. With such procedures, the amine-carbonyl intermediate represented by the general formula (5) can be produced at a high yield. The alkyl halide represented by the general formula (4-1) as a material of the Friedel-craft acylating reagent is preferably used in an amount of from 1.0 to 1.2 mol equivalent relative to the amine compound represented by the general formula (3). The carboxylic acid anhydride represented by the general formula (4-2) is used preferably in an amount of from 1.0 to 1.2 mol equivalent relative to the amine compound represented by the general formula (3). The aqueous alkaline solution to be used for the hydrolysis can include, for example, an aqueous sodium hydride solution and aqueous potassium oxide solution.

Then, the obtained amine-carbonyl intermediate represented by the general formula (5) is reacted with a Grignard reagent obtained by processing an allyl halide represented by the following general formula (6-1) or a general formula (6-2) with a metallic magnesium to produce the amine compound represented by the general formula (1). In the Grignard reaction, when the allyl halide represented by the general formula (6-1) is used, among the amine compounds represented by the general formula (1), an amine-butadiene compound in which n represents 1 can be produced. When the allyl halide represented by the general formula (6-2) is used, among the amine compounds represented by the general formula (1), an amine-hexatriene compound in which n represents 2 can be produced.

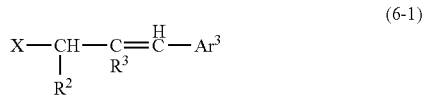

(6-1)

(wherein X represents a halogen atom, and $Ar^3$, $R^2$ and $R^3$ have the same meanings as those in the general formula (1)).

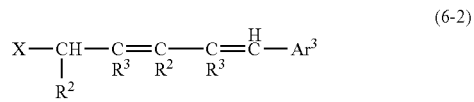

(6-2)

(wherein X represents a halogen atom, $Ar^3$, $R^2$ and $R^3$ have the same meanings as those in the general formula (1)).

The Grignard reaction is conducted, for example, as follows. The allyl halide represented by the general formula (6-1) or the general formula (6-2) and a metal magnesium are added substantially each in an equimolar amount in an appropriate solvent to prepare a Grignard reagent. A solvent to be used can include, for example, aromatic hydrocarbons such as toluene and xylene, ethers such as diethyl ether, tetrahydrofuran (abbreviated as THF) and ethylene glycol dimethyl ether. Preferably, these solvents are used while being dehydrated with metallic sodium and the like. An amine-carbonyl intermediate represented by the general formula (5) is added under cooling in the thus prepared solution in which the Grignard reagent is prepared and stirred under a room temperature or under heating at from 30° C. to 60° C. for 2 to 8 hours. The allyl halide represented by the general formula (6-1) or the general formula (6-2) as a material of the Grignard reagent is preferably used in an amount of from 1.1 to 1.2 mol equivalent relative to the amine-carbonyl intermediate represented by the general formula (5). The amine compound represented by the general formula (1) can thus be produced at a high yield.

In the production process for the amine compound of the invention, since the amine compound represented by the general formula (1) can be produced without using phosphoric reaction reagent which gives large burden to the global environments, the liquid wastes formed in the course of the production process give less burden on the global environment and can be disposed easily, with less expense necessary for the disposal of the liquid wastes. Accordingly, the production cost for the amine compound represented by the formula (1) can be lowered as described above.

Further, the amine compound of the invention represented by the general formula (1) can be isolated and purified easily from the reaction mixture by ordinary separation means, for example, a solvent extraction method, recrystallization method or column chromatography.

The electrophotographic photoreceptor according to the invention (hereinafter simply referred to as a photoreceptor) uses the amine compound of the invention represented by the general formula (1), preferably an amine butadiene compound represented by the general formula (2) described above as a charge-transporting substance, and it involves various embodiments. Description is to be made specifically below with reference to the drawings.

FIG. 1 is a fragmentary cross sectional view schematically showing the constitution of the electrophotographic photoreceptor according to a first embodiment of the invention. The electrophotographic photoreceptor 1 of this embodiment includes a cylindrical conductive support 11 made of a conductive material, a charge-generating layer 12 containing a charge-generating substance, and a charge-transporting layer 13 containing a charge-transporting substance. The charge-generating layer 12 is a layer laminated on the outer circumferential surface of the conductive support 11. The charge-transporting layer 13 is a layer laminated further on the charge-generating layer 12. The charge-generating layer 12 and the charge-transporting layer 13 constitute the photosensitive layer 14. That is, the photoreceptor 1 is a laminated type photoreceptor.

The conductive support 11 has a role as an electrode for the photoreceptor 1, as well as functions as a support member for other layers 12 and 13. Further, while the shape of the conductive support 11 is cylindrical in a case of the photoreceptor 1, it is not limited thereto, but may be elliptic, sheet-like or endless belt like shape.

The electroconductive materials constituting the conductive support 11 can include, for example, metal element such as aluminum, copper, zinc, titanium, etc., and an alloy such as an aluminum alloy and stainless steel, etc. It is not limited to those metal materials, but those prepared by laminating a metal foil, vapor depositing a metal material or vapor depositing or coating a layer of a conductive compound such as conductive polymers, tin oxide, indium oxide, etc., on the surface of polymeric materials such as polyethylene terephthalate, nylon or polystyrene, etc., hard paper, or glass may also be used. Such conductive materials are used while being formed into a predetermined shape.

The surface of the conductive support 11 may optionally be subjected to an anodizing coating film treatment, a surface treatment with a chemical or hot water, etc. a coloring treatment, or a random reflection treatment such as of surface roughening within a range of giving no effects on the picture quality. In an electrophotographic process using a laser as a light source for exposure, since the wavelength of the laser light is uniform, the laser light reflected on the surface of the photoreceptor and the laser light reflected in the inside of the photoreceptor cause interference, and interference fringes caused by the interference sometimes appear on the image to cause image defects. The image defects caused by the interference of the coherent laser light with uniform wavelength can be prevented by applying the treatment described above to the surface of the conductive support 11.

The charge-generating layer 12 contains a charge-generating substance which generates charges by absorbing light as a main component. Examples of effective substances as the charge-generating substance can include azo pigments such as monoazo pigments, bisazo pigments and trisazo pigments, indigo pigments such as indigo and thioindigo, perylene pigments such as perylene imide and polylenic acid anhydride, polycyclic quinone pigments such as anthraquinone and pirenequinone, phthalocyanine pigments such as metal phthalocyanine and non-metal phthalocyanine, squalirium dyes, pyrilium salts and thiopyrilium salts, organic photoconductive materials such as triphenyl methane dyes and inorganic photoconductive materials such as selenium and amorphous silicon. Those charge-generating substances may be used alone or two or more of them may be used in combination.

Among the charge-generating substances described above, an oxotitanium phthalocyanine compound represented by the following general formula (A) is preferably used.

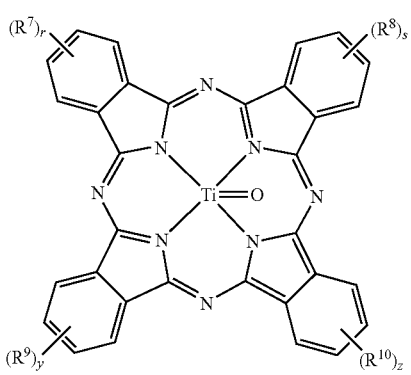

(A)

In the general formula (A), $R^7$, $R^8$, $R^9$ and $R^{10}$ each represents a hydrogen atom, a halogen atom, an alkyl group or alkoxy group, r, s, y and z each represents an integer of from 0 to 4.

It is preferred that the oxotitanium phthalocyanine compound represented by the general formula (A) has a specific crystal structure, and especially, it is optimum to use an oxotitanium phthalocyanine compound having a crystal structure showing a distinct diffraction peak at least at a Bragg angle 2θ (error: 2θ±0.2°) of 27.2° in an X-ray diffraction spectrum relative to Cu—Kα characteristic X-ray (wavelength: 1.54 Å). Incidentally, in the specification of the invention, the Bragg angle 2θ is an angle formed between incident X ray and diffraction X ray, so called a diffraction angle.

Since the oxotitanium phthalocyanine compound represented by the general formula (A) is a charge-generating substance having a high charge generation efficiency and charge injection efficiency. Therefore, the oxotitanium phthalocyanine compound generates a great amount of charges upon absorption of light and injects the generated charges efficiently to the charge-transporting substance contained in the charge-transporting layer 13 without storing them in the inside. Further as described above, since the amine compound represented by the general formula (1) of high charge-transporting ability is used for the charge-transporting substance contained in the charge-transporting layer 13, the charges generated from the oxotitanium phthalocyanine compound represented by the general formula (A) by light absorption are efficiently injected to the amine compound represented by the general formula (1) and transported smoothly to the surface of the photosensitive layer 14. Accordingly, an electrophotographic photoreceptor 1 of high sensitivity and high resolution can be obtained by using the oxotitanium phthalocyanine compound represented by the general formula (A) as the charge-generating substance and the amine compound of the invention represented by the general formula (1) as the charge-transporting substance.

The oxotitanium phthalocyanine compound represented by the general formula (A) can be produced by a production process known so far, such as a process described in "Phthalocyanine Compounds" written by Moser and Thomas. For example, among oxotitanium phthalocyanine compounds represented by the general formula (A), an oxotitanium phthalocyanine in which $R^7$, $R^8$, $R^9$ and $R^{10}$ each represents a hydrogen atom can be obtained by heat-melting phthalonitrile and titanium tetrachloride, or by reacting them under heating in an appropriate solvent such as α-chloronaphthalene to synthesize a dichlorotitanium phthalocyanine, and then hydrolyzing the same with a base or water. Further, the oxotitanium phthalocyanine can also be produced by reacting isoindoline and titanium tetraalkoxide such as tetrabuthoxy titanium in an appropriate solvent such as an N-methyl pyrrolidone.

The charge-generating substance may be used in combination with a sensitizing dye such as triphenyl methane dyes typically represented by methyl violet, crystal violet, night blue and Victoria blue, acridine dyes represented by erythrocin, rhodamine B, rhodamine 3R, acridine orange and flaveosin, thiazine dyes represented by methylene blue and methyl green, oxazine dyes represented by capriblue and Meldora's blue, cyanine dyes, styryl dyes, pyrylium salt dyes or thiopyrylium salt dyes.

The method of forming the charge-generating layer 12 can include a method of vapor-depositing the charge-generating substance on the surface of the conductive support 11 or a method of coating a coating solution for charge-generating layer obtained by dispersing the charge-generating substance described above in an appropriate solvent on the surface of the conductive support 11. Among them, preferably used is a method of dispersing the charge-generating substance in a binder resin solution obtained by mixing a binder resin as a binder in a solvent by a method known so far to prepare a coating solution for charge-generating layer and coating the obtained coating solution on the surface of the conductive support 11. Explanation will be made to the method below.

A binder resin to be used for the charge-generating layer 12 can include, for example, resins such as polyester resin, polystyrene resin, polyurethane resin, phenol resin, alkyd resin, melamine resin, epoxy resin, silicone resin, acryl resin, methacryl resin, polycarbonate resin, polyarylate resin, phenoxy resin, polyvinyl butyral resin and polyvinyl formal resin, and copolymer resins containing two or more repetitive units constituting these resins. Specific examples of the copolymer resin can include insulative resins such as vinyl chloride-vinyl acetate copolymer resin, vinyl chloride-vinyl acetate-maleic acid anhydride copolymer resin and acrylonitrile-styrene copolymer resin. The binder resin is not limited to them, but a resin generally used as a binder resin can be used. These resins can be used alone or two or more of them may be used as a mixture.

As a solvent for the coating solution for charge-generating layer, a halogenated hydrocarbon such as dichloromethane or dichloroethane, ketones such as acetone, methyl ethyl ketone or cyclohexanone, esters such as ethyl acetate or butyl acetate, ethers such as tetrahydrofuran (THF) or dioxane, alkylethers of ethylene glycol such as 1,2-dimethoxyethane, aromatic hydrocarbons such as benzene, toluene or xylene, or aprotonic polar solvents such as N,N-dimethyl formamide or N,N-dimethylacetoamide, etc., are used. Among the solvents, halogen free organic solvents are preferably used in view of global environments. Those solvents may be used alone or two or more of them may be mixed and used as a mixed solvent.

In the charge-generating layer 12 constituted by containing the charge-generating substance and the binder resin, the ratio W1/W2 for weight W1 of the charge-generating substance and weight W2 of the binder resin is preferably ten hundredths (10/100) or more and ninety-nine hundredths (99/100) or less. In a case where the ratio W1/W2 is less than 10/100, the sensitivity of the photoreceptor 1 is lowered. In a case where the ratio W1/W2 exceeds 99/100, not only the film strength of the charge-generating layer 12 is lowered but also the dispersibility of the charge-generating substance is lowered to increase the coarse particles. Therefore, surface charges in the portions other than those to be eliminated by exposure are decreased to increase image defects, particularly, fogging of images referred to as black spots formed as minute black spots by the deposition of the toner on the white background. Accordingly, the preferred range for the ratio W1/W2 was defined as 10/100 or more and 99/100 or less.

The dispersing machine used upon dispersion of the charge-generating substance in the binder resin solution can include, for example, ball mill, sand mill, attritter, vibration mill and supersonic wave dispersing machine.

The dispersing machine used upon dispersion of the charge-generating substance in the binder resin solution can include, for example, a paint shaker, ball mill or sand mill. As the dispersion condition in this case, appropriate conditions are selected so that impurities are not mixed, for example, by abrasion of members constituting a vessel and a dispersing machine to be used.

The coating method of the coating solution for charge-generating layer can include, for example, a spray method, bar coat method, roll coat method, blade method, wringing method or a dip coating method. Among the coating methods, an optimal method can be selected while taking the physical property of coating and productivity into consideration. Among the coating methods, particularly, the dip coating method is relatively simple and excellent in view of the productivity and the cost, so that this is used frequently in a case of producing electrophotographic photoreceptors. The dip coating method is a method of dipping a substrate to a coating tank filled with a coating solution and then pulling up it at a constant speed or a successively changing speed thereby forming a layer on the surface of the substrate. In the apparatus used for the dip coating method, a coating solution dispersion apparatus typically represented by a supersonic wave generation apparatus may also be provided.

The thickness of the charge-generating layer 12 is, preferably, 0.05 µm or more and 5 µm or less, more preferably, 0.1 µm or more and 1 µm or less. In a case where the thickness of the charge-generating layer is less than 0.05 µm, the light absorption efficiency is lowered to lower the sensitivity of the photoreceptor 1. In a case where the thickness of the charge-generating layer 12 exceeds 5 µm, charge transfer inside the charge-generating layer 12 forms a rate determining step in the process of eliminating the surface charges of the photosensitive layer 14 to lower the sensitivity of photoreceptor 1. Accordingly, a suitable range for the thickness of the charge-generating layer 12 is defined as 0.05 µm or more and 5 µm or less.

The charge-transporting layer 13 is provided on the charge-generating layer 12. The charge-transporting layer 13 can be constituted by incorporation of a charge-transporting substance having a function of accepting charges generated from the charge-generating substance contained in the charge-generating layer 12 and transporting them and a binder resin for binding the charge-transporting substance. As the charge-transporting substance, the amine compound of the invention represented by the general formula (1), preferably, the amine-butadiene compound represented by the general formula (2) can be used as described above.

The amine compound of the invention, represented by the general formula (1), preferably, the amine-butadiene compound represented by the general formula (2) as a charge-transporting substance is incorporated in the charge-transporting layer 13. Thereby, a highly reliable photoreceptor 1 which is excellent in electric characteristics such as chargeability, sensitivity and light responsiveness, which does not deteriorate favorable electric characteristics even when the surrounding circumstances such as temperature and humidify are changed and even when it is used repetitively or when it is exposed to external light can be realized. Further, since the photosensitive layer 13 can be provided with excellent wear resistant property to improve the printing resistance of the photosensitive layer 14, the photoreceptor 1 is excellent also in the mechanical durability. Accordingly, the photoreceptor 1 does not suffer from deterioration of the picture quality in the formed images over a long time even when it is used under low temperature circumstances and in a case where it is used for a high speed electrophotographic process.

As described above, the production cost for the amine compound represented by the formula (1), particularly, the amine-butadiene compound represented by the general formula (2) is low, a highly reliable photoreceptor 1 excellent in the electric characteristic, circumstantial stability, and electrical and mechanical durability as described above can be produced at a low production cost by using the amine compound represented by the general formula (1), preferably, the amine-butadiene compound represented by the general formula (2) as the charge-transporting substance.

The amine compound represented by the general formula (1) are used being selected, for example, from the group consisting of exemplified compounds shown in Tables 1 to 4 described above alone or in admixture of two or more of them.

Further, the amine compound represented by the general formula (1) may be used while being mixed with other charge-transporting substances. Other charge-transporting substances to be used while being mixed with the amine compound represented by the general formula (1) can include, for example, an enamine compound such as an enamine-styryl derivative, enamine-hydrazone derivative, enamine-butadiene derivative and enamine-hexatriene derivative, and carbazole derivative, oxazole derivative, oxadiazole derivative, thiazole derivative, thiadiazole derivative, triazole derivative, imidazole derivative, imidazolone derivative, imidazolidine derivative, bisimidazolidine derivative, styryl compound, hydrazone compound, polycyclic aromatic compound, indole derivative, pyrazoline derivative, oxazolone derivative, benzimidazole derivative, quinazoline derivative, benzofuran derivative, acrydine derivative, phenadine derivative, aminostylbene derivative, triarylamine derivative, triarylmethane derivative, phenylene diamine derivative, stylbene derivative and benzidine derivative. In addition, polymers having groups derived from those compounds in the main chain or on side chains, for example, poly (N-vinyl carbazole), poly(1-vinylpyrene) and poly(9-vinylanthracene) and the like are included.

For the binder resin constituting the charge-transporting layer 13, those having excellent compatibility with the charge-transporting substance are selected. Specific examples of them can include, for example, a vinyl polymer resin such as polymethyl methacrylate resin, polystyrene resin or polyvinyl chloride resin, and a copolymer resin containing two or more repetitive units constituting them, and polycarbonate resin, polyester resin, polyester carbonate resin, polysulfone resin, phenoxy resin, epoxy resin, silicone resin, polyacrylate resin, polyamide resin, polyether resin, polyurethane resin, polyacrylamide resin and phenol resin. In addition, the resin can include a thermosetting resin formed by partially crosslinking the resins. The resin may be used alone or two or more of them may be used as a mixture. Among the resins described above, the polystyrene resin, polycarbonate resin, polyacrylate resin or polyphenyl oxide is used suitably, having a volumic resistivity of $10^{13}$ Ω·cm or more, being excellent in electric insulation property, and also excellent in the film-forming property and potential characteristic.

In the charge-transporting layer 13, a ratio A/B between the weight A for the amine compound represented by the general formula (1) contained as the charge-transporting substance and the weight B for the binder resin is ten thirtieths (10/30) or more and ten twelfths (10/12) or less. By determining the ratio A/B to 10/30 or more and 10/12 or less and incorporating the binder resin at a high ratio in the charge-transporting layer 13, the printing resistance of the charge-transporting layer 13 can be improved. Accordingly, the mechanical durability of the photoreceptor 1 can be improved further by the synergistic effect with the excellent wear resistant property of the charge-transporting layer 13 provided by the incorporation of the amine compound represented by the general formula (1).

In a case where the ratio A/B is determined as 10/12 or less and the ratio of the binder resin is increased, the ratio of the amine compound represented by the general formula (1) contained as the charge-transporting substance is lowered as a result. In a case of using a charge-transporting substance known so far, when the ratio between the weight of the charge-transporting substance and the weight of the binder resin in the charge-transporting layer 13 (charge-transporting substance/binder resin) is determined as: 10/12 or less in the same manner, the light responsiveness becomes insufficient and image defects sometimes occur. Since the amine compound represented by the general formula (1) has, however, high charge-transporting ability, even when the ratio A/B is determined as 10/12 or less and the ratio of the binder resin in the charge-transporting layer 13 is increased, the photoreceptor 1 shows a sufficiently high light responsiveness and can provide a high image quality. Namely, the photoreceptor 1 having a high light responsiveness and excellent, particularly, in mechanical durability can be obtained while determining the ratio A/B as 10/30 or more and 10/12 or less without lowering the light responsiveness.

In a case where the ratio A/B is less than 10/30 and the ratio of the binder resin becomes too high, the sensitivity of the photoreceptor 1 is lowered. Further, in a case where the charge-transporting layer 13 is formed by a dip coating method, since the viscosity of the coating solution is increased to lower the coating velocity, the productivity is extremely worsened. Further, in a case where the amount of a solvent in the coating solution is increased in order to suppress the increase of the viscosity of the coating solution, brushing phenomenon occurs to cause clouding in the formed charge-transporting layer 13. Further, in a case where the ratio A/B exceeds 10/12, and the ratio of the binder resin becomes too low, the printing resistance of the photosensitive layer 14 is lowered to increase the amount of reduction of the film, and the chargeability of the photoreceptor 1 is lowered. Accordingly, a preferred range for the ratio A/B is determined as 10/30 or more and 10/12 or less.

In the charge-transporting layer 13, various kinds of additives may optionally be added. For example, in order to improve the film-forming property, flexibility or surface smoothness, a plasticizer, a leveling agent or the like may be added to the charge-transporting layer 13. The plasticizer can include, for example, a dibasic acid ester such as phthalic acid ester, fatty acid ester, phosphoric acid ester, chlorinated paraffin and epoxy plasticizer. The leveling agent can include, for example, a silicone-based leveling agent.

In order to enhance the mechanical strength and improve the electric characteristics, fine particles of an inorganic compound or organic compound may be added to the charge-transporting layer 13.

The charge-transporting layer 13 is formed by dissolving or dispersing the charge-transporting substance containing the amine compound represented by the general formula (1), a binder resin and, optionally, the additive described above in an appropriate solvent to prepare a coating solution for charge-transporting layer and coating the obtained coating solution on the charge-generating layer 12, in the same manner as in the case of forming the charge-generating layer 12 by coating.

The solvent for the coating solution for charge-transporting layer can include, for example, aromatic hydrocarbons such as benzene, toluene, xylene and monochlorbenzene, halogenated hydrocarbons such as dichloromethane and dichloroethane, ethers such as tetrahydrofuran (THF), dioxane and dimethoxy methylether, and aprotonic polar solvents such as N,N-dimethyl formamide. The solvents may be used alone or two or more of them may be used as a mixture. In addition, the solvent may be used optionally with addition of a solvent such as alcohols, acetonitrile or methyl ethyl ketone to the solvent. Among the solvents, halogen free organic solvents are preferably used in view of the global environment.

The coating method for the coating solution for charge-transporting layer can include, for example, a spray method, bar coat method, roll coat method, blade coating method, wringing method and dip coating method. Among the coating methods, since the dip coating method is particularly excellent in various points as described above, it has been used preferably in a case of forming the charge-transporting layer 13.

The thickness of the charge transfer layer 13 is preferably 5 μm or more and 50 μm or less, more preferably, 10 μm or more and 40 μm or less. In a case where the thickness of the charge-transporting layer 13 is less than 5 μm, the charge retainability is lowered. In a case where the thickness of the charge-transporting layer 13 exceeds 50 μm, the resolution of the photoreceptor 1 is lowered. Accordingly, a preferred range for the thickness of the charge-transporting layer is determined as 5 μm or more and 50 μm or less.

The charge-generating layer 12 and the charge-transporting layer 13 thus formed are laminated to constitute a photosensitive layer 14. Since a charge-generating function and a charge-transporting function are thus shared on separate layers and an optimal material can be selected for each of the charge-generating function and the charge-transporting function as a material constituting each layer. Therefore, the photoreceptor 1 having particularly excellent electric characteristics such as chargeability, sensitivity and light responsiveness and further having particularly high durability with increased stability upon repetitive use can be attained.

For each layer of the photosensitive layer 14, namely, the charge-generating layer 12 and the charge-transporting layer 13, one or more electron accepting substances and sensitizers such as dyes may be added in order to improve the sensitivity and suppress the increase of the residual potential and fatigues due to repetitive use.

As the electron accepting substance, for example, acid anhydrides such as succinic acid anhydride, maleic acid anhydride, phthalic acid anhydride and 4-chloronaphthalic acid anhydride, etc., cyano compounds such as tetracyano ethylene, terephthal malone dinitrile, aldehydes such as 4-nitrobenzaldehyde, etc. anthraquinones such as anthraquinone and 1-nitroanthraquinone, polycyclic or heterocyclic nitro compounds such as 2,4,7-trinitrofluolenone, 2,4,5,7-tetranitrofluolenone, etc. or electron attracting materials such as diphenoquinone compounds can also be used. In addition, those electron attracting materials, which are polymerized, can also be used.

As the dye, organic photoconductive compounds such as xanthene dyes, thiazine dyes, triphenylmethane dyes, quinoline dyes or copper phthalocyanine, etc. can be used. The organic photoconductive compounds function as optical sensitizers.

In addition, an antioxidant or an ultraviolet absorber may be added to each layer 12, 13 of the photosensitive layer 14. Particularly, it is preferred to add an antioxidant or an ultraviolet absorber to the charge-transporting layer 13. This can improve the potential characteristic. Further, stability of the coating solution upon forming each of the layers by coating can be enhanced. In addition, fatigue of the photoreceptor 1 due to repetitive use can be moderated to improve the electric durability.

As the antioxidant, a phenol compound, hydroquinone compound, tocopherol compound or amine compound is used. Among them, a hindered phenol derivative or hindered amine derivative or a mixture thereof is preferably used. The amount of the antioxidant to be used is preferably 0.1 parts by weight or more and 50 parts by weight or less based on 100 parts by weight of the charge-transporting substance. In a case where the amount of the charge-transporting substance is less than 0.1 parts by weight based on 100 parts by weight of the charge-transporting substance, no sufficient effects can be obtained for improving the stability of the coating solution and improving the durability of the photoreceptor. In a case where it is more than 50 parts by weight, this gives undesired effects on the characteristics of the photoreceptor. Accordingly, a preferred range for the amount of the antioxidant to be used is determined as 0.1 parts by weight or more and 50 parts by weight or less based on 100 parts by weight of the charge-transporting substance.

FIG. 2 is a fragmentary cross sectional view schematically showing the constitution of an electrophotographic photoreceptor 2 according to a second embodiment of the invention. The electrophotographic photoreceptor 2 of this embodiment is similar to the electrophotographic photoreceptor 1 of the first embodiment shown in FIG. 1, in which corresponding portions carry identical reference numerals for which explanations are to be omitted.

In the electrophotographic photoreceptor 2, it is to be noted that an intermediate layer 15 is provided between a conductive substrate 11 and a photosensitive layer 14.

In a case where the intermediate layer 15 is not present between the conductive substrate 11 and the photoreceptor 14, charges are injected from the conductive substrate 11 to the photosensitive layer 14, the chargeability of the photosensitive layer 14 is lowered, and surface charges at a portion other than the portion to be eliminated by exposure are decreased to sometimes cause defects such as fogging to images. Particularly, in a case of forming images by using a reversal development process, toners are deposited to a portion where the surface charges are decreased by exposure to form toner images. Accordingly, when the surface charges are decreased by the factors other than exposure, the toners are deposited to a white background and form minute black spots to case fogging to the images referred to as black pots to sometimes deteriorate the picture quality remarkably. That is, in a case where the intermediate layer 15 is not present between the conductive substrate 11 and the photosensitive layer 14, the chargeability is lowered in a minute region caused by the defects of the conductive substrate 11 or the photosensitive layer 14 to sometimes cause fogging of images such as black spots to result in remarkable image defects.

In the electrophotographic photoreceptor 2 of this embodiment, since the intermediate layer 15 is provided between the conductive substrate 11 and the photosensitive layer 14 as described above, injection of charges from the conductive substrate 11 to the photosensitive layer 14 can be prevented. Accordingly, lowering of the chargeability of the photosensitive layer 14 can be prevented, decrease of the surface charges in the portion other than the portion to be eliminated by exposure can be suppressed and formation of defects to images such as fogging can be prevented.

Further, since the defects on the surface of the conductive substrate 11 is covered by disposing the intermediate layer 15 thereby capable of obtaining a uniform surface, film-forming property of the photosensitive layer 14 can be improved. Further, since the intermediate layer 15 functions as an adhesive for the conductive support 11 and the photosensitive layer 14, peeling of the photosensitive layer 14 from the conductive support 11 can be prevented.

For the intermediate layer 15, a resin layer made of various resin materials or an alumite layer, etc. is used.

A resin material for constituting the resin layer can include, for example, resins such as polyethylene resin, polypropylene resin, polystyrene resin, acrylic resin, vinyl chloride resin, vinyl acetate resin, polyurethane resin, epoxy resin, polyester resin, melamine resin, silicone resin, polyvinyl butyral resin and polyamide resin and copolymer resins containing two or more repeating units constituting those resins. Further, they can also include casein, gelatin, polyvinyl alcohol and ethyl cellulose. Among those resins, the polyamide resin is preferably used, and in particular, alcohol-soluble nylon resin can be preferably used. Preferred examples of the alcohol-soluble nylon resin can include, so called copolymerized nylon prepared by copolymerizing, for example, 6-nylon, 6,6-nylon, 6,10-nylon, 11-nylon, 2-nylon and 12-nylon, and resins prepared by chemically modifying nylon, such as N-alkoxy methyl-modified nylon and N-alkoxyethyl modified nylon.

The intermediate layer 15 may contain particles such as metal oxide particles. By incorporation of the particles in the intermediate layer, the volumic resistance value of the intermediate layer 15 can be controlled, the effect of preventing the injection of charges from the conductive substrate 11 to the photosensitive layer 14 can be enhanced, and the electric characteristics of the photoreceptor 2 can be maintained under various circumstances.

The metal oxide particles can include, for example, particles of titanium oxide, aluminum oxide, aluminum hydroxide, tin oxide, etc.

The intermediate layer 15 is formed, for example, by dissolving or dispersing the resin described above in an appropriate solvent to prepare a coating solution for intermediate layer, and coating the coating solution on the surface of the conductive substrate 11. In a case of incorporating particles such as metal oxide particles described above in the intermediate layer 15, the intermediate layer 15 can be formed by dispersing the particles in a resin solution obtained by dissolving the resin described above in an appropriate solvent to prepare a coating solution for intermediate layer, and coating the coating solution on the surface of the conductive substrate 11.

For the solvent of the coating solution for intermediate layer, water or various kinds of organic solvents or mixed solvents of them may be used. For example, a single solvent of water, methanol, ethanol or butanol or a mixed solvent such as of water and alcohol, two or more kinds of alcohols, acetone or dioxolane and alcohols, and chlorine type solvent such as dichloroethane, chloroform or trichloroethane and alcohols are used. Among the solvents, halogen free organic solvents are preferably used in view of the global environment.

For the method of dispersing the particles in a resin solution, ordinary methods including the use of a ball mill, sand mill, attritor, vibration mill, ultrasonic wave dispersing machine or paint shaker can be used.

In the coating solution for intermediate layer, a ratio C/D between the weight C for the sum of the resin and the metal oxide and the weight D for the solvent to be used in the coating solution for intermediate layer is preferably from 1/99 to 40/60, more preferably, from 2/98 to 30/70. Further a ratio E/F between the weight E of the resin and the weight F of the metal oxide is preferably from 90/10 to 1/99 and more preferably, from 70/30 to 5/95.

The method for coating the coating solution for intermediate layer can include, for example, a spray method, bar coat method, roll coat method, blade method, wringing method or a dip coating method. In particular, the dip coating method is suitably used among them also in a case of forming the intermediate layer 15, since it is relatively simple and excellent in view of the productivity and the cost.

The film thickness of the intermediate layer 15 is preferably 0.01 μm or more and 20 μm or less, more preferably, 0.05 μm or more and 10 μm or less. In a case where the intermediate layer 15 has a film thickness of less than 0.01 μm, it does not substantially function as the intermediate layer 15, so that a uniform surface cannot be obtained by covering the defects of the conductive support 11, the injection of charges from the conductive support 11 to the photosensitive layer 14 can not be prevented, to result in lowering of the chargeability of the photosensitive layer 14. Increase of the film thickness of the intermediate layer 15 to more than 20 μm is undesirable since the formation of the intermediate layer 15 becomes difficult in a case of forming the intermediate layer 15 by the dip coat method, making it impossible to form the photosensitive layer 14 uniformly on the intermediate layer 15, and the sensitivity of the photoreceptor 2 is lowered. Accordingly, a preferred range for the film thickness of the intermediate layer 15 is determined to 0.01 μm or more and 20 μm or less.

Also in this embodiment, various kinds of additives such as plasticizers, leveling agents or fine particles of organic or inorganic compounds may be added in the same manner as in the first embodiment. Further, electron accepting substances or additives, for example, sensitizers such as dyes, antioxidants or UV-ray absorbers can be added to each of layers 12, 13 of the photosensitive layer 14.

FIG. 3 is a fragmentary cross sectional view schematically showing the constitution of an electrophotographic photoreceptor 3 according to a third embodiment of the invention. The electrophotographic photoreceptor 3 of this embodiment shown in FIG. 2 is similar to the electrophotographic photoreceptor 2 of the second embodiment in which corresponding portions carry identical reference numerals, for which explanations are to be omitted.

In the electrophotographic photoreceptor 3, it is to be noted that a photosensitive layer 140 is constituted with a single layer containing a charge-generating substance and a charge-transporting substance. That is, the electrophotographic photoreceptor 3 is a single layer type photoreceptor.

The single layer type photoreceptor 3 of this embodiment is preferable as a photoreceptor for use in a positively charged type image forming apparatus with less generation of ozone, and since the photosensitive layer 140 to be coated has only one layer, it is excellent compared with the laminated photoreceptor 1, 2 of the first embodiment or the second embodiment in view of the manufacturing cost and the yield.

Also in this embodiment, various kinds of additives such as plasticizers, leveling agents, fine particles of inorganic compounds or organic compounds, sensitizers such as electron accepting substances or dyes, antioxidants or UV-ray absorbers may be added to the photosensitive layer 140 in the same manner as in the first embodiment.

The photosensitive layer 140 is formed by the method identical with that for the charge-transporting layer 13 provided to the electrophotographic photoreceptor 1 of the first embodiment. For example, a coating solution for photosensitive layer is prepared by dissolving or dispersing the charge-generating substance, the charge-transporting substance containing the amine compound represented by the general formula (1), preferably, the amine-butadiene compound represented by the general formula (2), the binder resin and, optionally, the additives described above into an appropriate solvent similar to that for the coating solution for charge-transporting layer. The coating solution for photosensitive layer is coated to the surface of the intermediate layer 15, for example, by a dip coating method. Thereby, the photosensitive layer 140 can be formed.

The ratio A'/B' between the weight A' of the amine compound represented by the general formula (1) and the weight B' of the binder resin in the photosensitive layer 140 is, preferably, 10/30 or more and 10/12 or less with the same reason as that for the ratio A/B between the weight A of the amine compound represented by the general formula (1) and the weight B of the binder resin in the charge-transporting layer 13 of the first embodiment.

The film thickness of the photosensitive layer 140 is, preferably, 5 μm or more and 100 μm or less, more preferably, 10 μm or more and 50 μm or less. In a case where the film thickness of the photosensitive layer 140 is less than 5 μm, the charge retainability of the surface of the photosensitive layer is lowered. In a case where the film thickness of the photosensitive layer 140 exceeds 100 μm, the productivity is lowered. Accordingly, a suitable range for the film thickness of the photosensitive layer 140 is defined as 5 μm or more and 100 μm or less.

The electrophotographic photoreceptor according to the invention is not restricted to the constitutions for the electrophotographic photoreceptors 1, 2 and 3 of the first embodiment to the third embodiment shown in FIG. 1 to FIG. 3, but it may be of any other different constitutions so long as the amine compound represented by the general formula (1) is contained in the photosensitive layer.

For example, it may be a constitution of providing a surface protective layer to the surface of the photosensitive layer 14 or 140. Provision of the surface protective layer on the surface of the photosensitive layer 14 or 140 further improves the mechanical durability of the photoreceptors 1, 2, and 3. Further, this can prevent undesired chemical effects of an active gas such as ozone and nitrogen oxide (NOx) generated by corona discharge upon charging the surface of the photoreceptor on the photosensitive layers 14 and 140, thereby enabling to improve the electrical durability of the photoreceptors 1, 2 and 3.

As the surface protective layer, a layer comprising, for example, a resin, an inorganic filler-containing resin or an inorganic oxide is used.

Then, the image forming apparatus having the electrophotographic photoreceptor according to the invention is to be described. The image forming apparatus according to the invention is not restricted to the content of the following descriptions.

Figure 4:
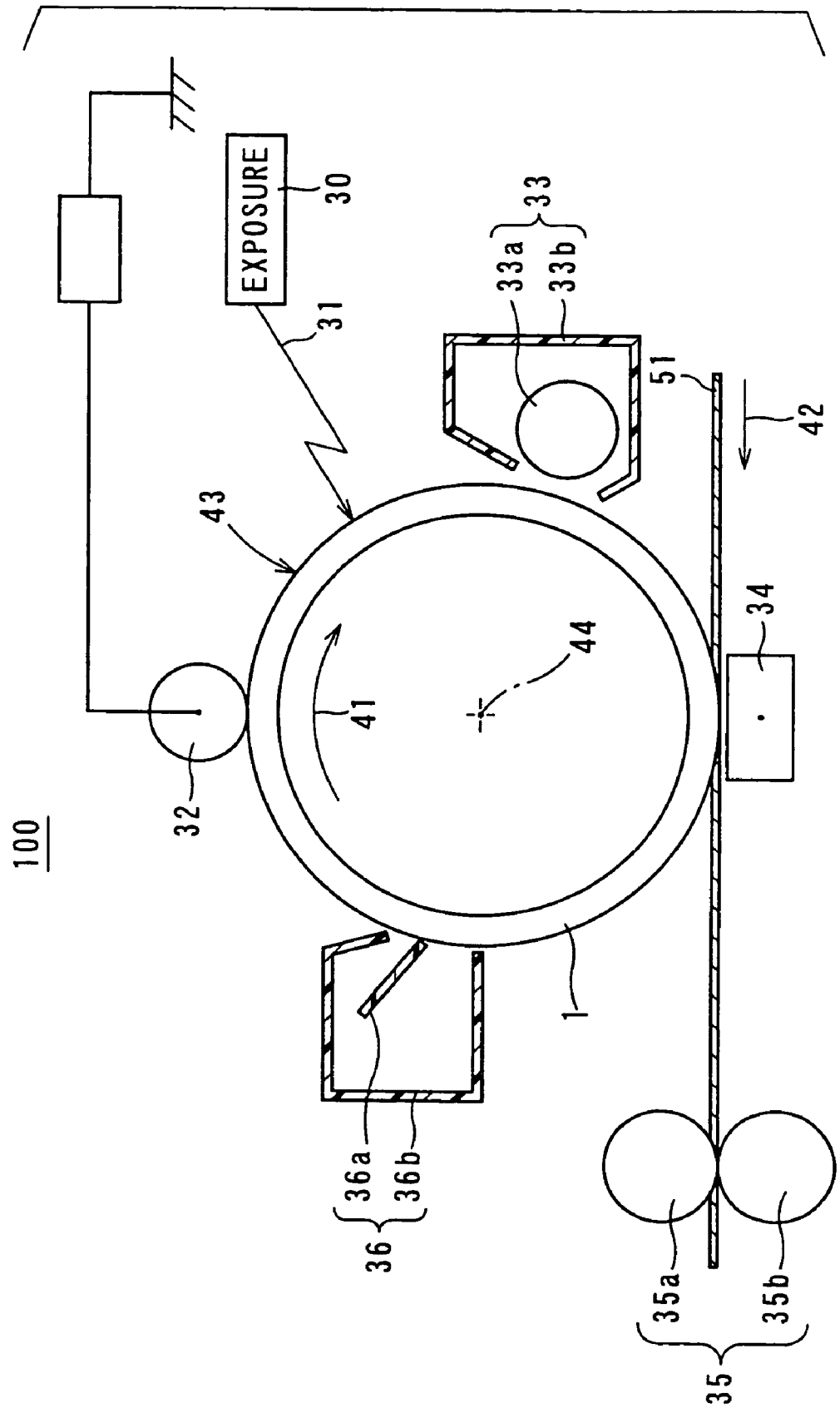
FIG. 4 is a side elevational view for the arrangement of a constitution of an image forming apparatus in a simplified manner according to an embodiment of the invention.

FIG. 4 is a side elevational view for the arrangement of a constitution of an image forming apparatus 100 in a simplified manner as an embodiment of the image forming apparatus according to the invention. The image forming apparatus 100 shown in FIG. 4 has mounted thereon the photosensitive material 1 shown in FIG. 1 described above as the first embodiment of the electrophotographic photoreceptor according to the invention. The constitution and the image forming operation of the image forming apparatus 100 are to be described with reference to FIG. 4.

The image forming apparatus 100 comprises the photoreceptor 1 supported rotationally to an apparatus main body not illustrated, not illustrated driving means for rotationally driving the photoreceptor 1 around a rotational axis 44 in the direction of an arrow 41. The driving means has, for example, a motor as a power source. The driving means transmits the power from the motor by way of a not illustrated gear to a support constituting the core of the photoreceptor 1 to rotationally drive the photoreceptor 1 at a predetermined circumferential speed.

At the periphery of the photoreceptor 1 are disposed a charger 32, exposure means 30, a developing device 33, a transfer device 34, and a cleaner 36 from the upstream to the downstream in the rotational direction of the photoreceptor 1 shown by the arrow 41 in this order. The cleaner 36 is disposed together with a charge elimination lamp not illustrated.

The charger 32 is charging means for uniformly charging the surface 43 of the photoreceptor 1 to a predetermined negative or positive potential. The charger 32 is contact type charging means such as a charging roller.

The exposure means 30 has, for example, a semiconductor laser or the like as a light source and exposes the charged surface 43 of the photoreceptor 1 by a light 31, for example, of a laser beam emitted in accordance with the image information from the light source, to thereby form electrostatic latent images on the surface 43 of the photoreceptor 1.

The developing device 33 is developing means for developing the electrostatic latent image formed on the surface 43 of the photoreceptor 1 by a developer thereby forming toner images as visible images. The developing device 33 comprises a developing roller 33a and a casing 33b. The developing roller 33a is disposed being opposed to the photoreceptor 1 for supplying toners to the surface 43 of the photoreceptor 1. The casing 33b rotationally supports the developing roller 33a around a rotational axis parallel with the rotational axis 44 of the photoreceptor 1 and stores a toner-containing developer in the inner space thereof.

The transfer device 34 is transfer means for transferring toner images formed on the surface 43 of the photoreceptor 1 from the surface 43 of the photoreceptor 1 onto a recording paper 51 as the transfer material. The transfer device 34 is non-contact type transfer means having charging means, for example, a corona discharger and giving electric charges at a polarity opposite to that of the toners on the recording paper 51 thereby transferring the toner images on the recording paper 51.

The cleaner 36 is cleaning means for cleaning the surface of the photoreceptor 1 after transfer of the toner images. The cleaner 36 comprises a cleaning blade 36a and a recovery casing 36b. The cleaning blade 36a is urged to the surface 43 of the photoreceptor 1 for peeling the toner remaining on the surface 43 of the photoreceptor 1 from the surface 43 after the transfer operation by the transfer device 34. The recovery casing 36b stores the toners peeled by the cleaning plate 36a.

Further, a fixing device 35 as fixing means for fixing the transferred images is provided in the direction along which recording paper 51 is transported after passage between the photoreceptor 1 and a transfer device 34. The fixing device 35 comprises a heating roller 35a having not illustrated heating means and a pressing roller 35b. The pressing roller 35b is disposed being opposed to the heating roller 35a and pressed by the heating roller 35a to thereby form an abutting portion.

Then, the image forming operation by the image forming apparatus 100 is to be described. At first, the photoreceptor 1 is rotationally driven by the driving means in the direction of the arrow 41 in accordance with the instruction from a not illustrated control section. Then, the surface 43 charges to a predetermined positive or negative potential by the charger 32 provided to the upstream, in the rotational direction, of the photoreceptor 1 relative to a focusing point of a light 31 from the exposure means 30.

Then, light 31 is irradiated to the charged surface 43 of the photoreceptor 1 from the exposure means 30 in accordance with the instruction from the control section. The light 31 from the light source is scanned repetitively in the longitudinal direction of the photoreceptor 1 as the main scanning direction based on the image information. When the photoreceptor 1 driven rotationally and the light 31 from the light source is caused to scan repetitively based on the image information, exposure can be applied corresponding to the image information to the surface 43 of the photoreceptor 1. The exposure decreases the surface charges for a portion irradiated with the light 31 thereby causing the difference between the surface potential for the portion irradiated with the light 31 and the surface potential for the portion not irradiated with the light 31. As a result, an electrostatic latent image is formed on the surface 43 of the photoreceptor 1. Further, in synchronization with exposure to the photoreceptor 1, the recording paper 51 is supplied by the conveyor means in the direction of an arrow 42 to the transfer position between the transfer device 34 and the photoreceptor 1.

Then, toners are supplied to the surface 43 of the photoreceptor 1 formed with the electrostatic latent image from the developing roller 33a of the developing device 33 situated downstream, in the rotational direction, of the photoreceptor 1 relative to the focusing point of the light 31 from the light source. This develops the electrostatic latent images, to form toner images as visible image on the surface 43 of the photoreceptor 1. When the recording paper 51 is supplied between the photoreceptor 1 and the transfer device 34, charges at a polarity opposite to that of the toners is given by the transfer device 34 to the recording paper 51, thereby transferring the toner images formed on the surface 43 of the photoreceptor 1 onto the recording paper 51.

The recording paper 51 transferred with the toner images are conveyed by the conveying means to the fixing device 35 and heated and pressed upon passage through the abutting portion between the heating roller 35a and the press roller 35b of the fixing device 35. This fixes the toner images of the recording paper 51 to the recording paper 51 to form firm images. The recording paper 51 thus formed with the images is exhausted by conveyor means to the outside of the image forming apparatus 100.

After transfer of the toner images to the recording paper 51, the photoreceptor 1 which is further rotated in the direction of the arrow 41 is frictionally rubbed and cleaned at the surface 43 with the cleaning blade 36a provided to the cleaner 36. The surface 43 of the photoreceptor 1 thus removed with the toners as described above is charge eliminated by the light from the charge elimination lamp, by which electrostatic latent images on the surface 43 of the photoreceptor 1 are eliminated. Then, the photoreceptor 1 further driven rotationally and a series of operations starting from the charging for the photoreceptor 1 again are repeated. As described above, images are formed continuously.

Since the photoreceptor 1 provided to the image forming apparatus 100 contains the amine compound of the invention represented by the general formula (1), preferably, the amine-butadiene compound represented by the general formula (2) as the charge-transporting substance in the photosensitive layer 14 as described above. Therefore, it is excellent in the electric characteristics such as the chargeability, the sensitivity and the light responsiveness, not suffering from the deterioration of favorable electric characteristics even when the surrounding circumstance such as temperature and humidity are changed or even when it is used repetitively and is also excellent in the mechanical durability. Accordingly, a highly reliable image forming apparatus 100 capable of stably forming images with no degradation of the picture quality over a long time under various circumstances can be attained. Further, since the photoreceptor 1 does not suffer from degradation of the picture quality to the formed images even when it is used in a high speed electrophotographic process, the image forming apparatus 100 can form high quality images at high speed. Further, since the electric characteristics of the photoreceptor 1 is not deteriorated even when it is exposed to external light, deterioration of the image quality attributable to the exposure of the photoreceptor 1 to external light for example during maintenance can be suppressed.

The image forming apparatus according to the invention is not restricted to the constitution of the image forming apparatus 100 shown in FIG. 4 described above, but any other different constitution may be adopted so long as the photoreceptor of the invention can be used.

For example, in the image forming apparatus 100 of this embodiment, while the charger 32 is contact type charging means, this is not restrictive but it may be non-contact type charging means such as the corona discharger. Further, while the transfer device 34 is non-contact type transfer means for conducting transfer without using a pressing force, this is not limitative but it may be contact type transfer means for conducting transfer utilizing the pressing force. As the contact type transfer means, it is possible to use those, for example, having a transfer roller. This kind of the transfer means presses the transfer roller to the photoreceptor 1 from the side opposite to the abutting surface of the recording paper 51 that abuts against the surface 43 of the photoreceptor 1 and applies a voltage to the transfer roller in a state of press contacting the photoreceptor 1 and the recording paper 51, thereby transfers the toner images on the recording paper 51.

The invention is to be described more specifically by way of examples but the invention is not restricted to them.

PREPARATION EXAMPLE

Preparation Example 1

Preparation of Exemplified Compound No. 1

Preparation Example 1-1

Preparation of Amine-carbonyl Intermediate Product 4.70 g (1.2 molar equivalent amount) of acetyl chloride was added gradually under ice cooling into 100 mL of anhydrous dichloromethane in which 8.0 g (1.2 molar equivalent amount) of aluminum chloride was suspended, stirred for about 30 min to prepare a Friedel-craft acylation reagent. 16.17 g (1.0 molar equivalent amount) of the amine compound represented by the following structural formula (7) was added gradually under ice-cooling into the solution. Then, it was gradually heated to raise the reaction temperature up to 30° C. and stirring was effected for 3 hours under heating so as to keep it at 30° C. After allowing the reaction solution to cool, it was added gradually to 400 mL of an aqueous 4N sodium hydroxide solution to cause precipitation. After separating resultant precipitates by filtration and washing sufficiently with water, it was re-crystallized in a mixed solvent of ethanol and ethyl acetate to obtain 19.7 g of a yellow powdery compound.

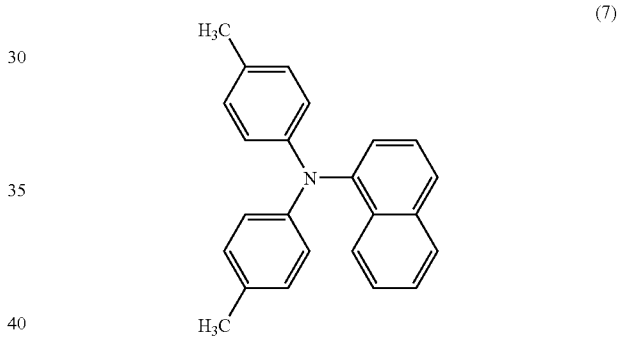

(7)

As a result of analyzing the resultant compound by Liquid Chromatography-Mass Spectrometry (abbreviated as LC-MS), since a peak corresponding to the molecular ion [M+H]+ in which a proton was added to the amine-carbonyl intermediate product represented by the following structural formula (8) (calculated value of molecular weight: 365.18) was observed at 366.2. It was confirmed that the resultant compound was an amine-carbonyl intermediate product represented by the structural formula (8) (yield: 92%). Further, from the result of LC-MS analysis, it was found that the purity of the resultant amine-carbonyl intermediate product was 98.1%.

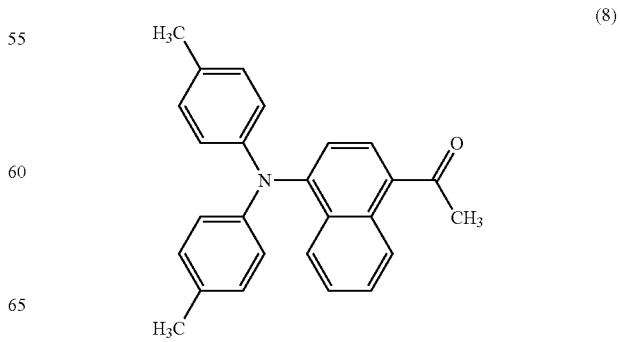

(8)

Preparation Example 1-2

Preparation of Exemplified Compound No. 1

1.94g (1.2 molar equivalent amount) of cinnamyl bromide represented by the following structural formula (9) and 240 mg of a metallic magnesium powder (1.2 molar equivalent amount) were added to 20 mL of anhydrous THF to prepare a Grignard reagent. 3.0 g (1.0 molar equivalent amount) of the amine carbonyl intermediate product represented by the structural formula (8) obtained in Preparation Example 1-1 was gradually added at 0° C. to the solution. Then, after leaving at a room temperature for 1 hour, it was heated to 40° C. and stirred while heating at 5 hours so as to be kept at 40° C. After allowing the reaction solution to cool, it was poured into excess methanol. Precipitates were recovered and dissolved in toluene to form a toluene solution. The toluene solution was transferred to a separable flask, washed with water and then an organic layer was taken out and the recovered organic layer was dried with magnesium sulfate. After drying, the organic layer removed with solids was concentrated and subjected to silica gel chromatography to obtain 3.46 g of yellow crystals.

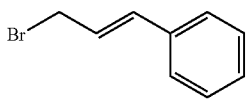

(9)

As a result of LC-MS analysis for the resultant crystals, since a peak corresponding to the molecular ion [M+H]+ in which a proton was added to the aimed amine-butadiene compound of Exemplified Compound No. 1 shown in Table 1 (calculated value of molecular weight: 465.25) was observed at 466.3. It was confirmed that the resultant crystal was an amine-butadiene compound of Exemplified Compound No. 1 (yield: 91%). Further, as the result of LC-MS analysis, it was found that the purity of the resultant amine-butadiene compound as the obtained Exemplified Compound No. 1 was 99.5%.

As described above, the amine-butadiene compound of Exemplified Compound No. 1 could be obtained without using a phosphorous reaction reagent, by synthesizing the amine-carbonyl intermediate product represented by the structural formula (8) by a Friedel-craft acylation reaction using acetyl chloride of the amine compound represented by the structural formula (7) and then conducting the Grignard reaction between the resultant amine-carbonyl intermediate product represented by the structural formula (8) and a Grignard reagent prepared from cinnamyl bromide represented by the structural formula (9) and metal magnesium.

Preparation Example 2

Preparation of Exemplified Compound No. 30

Friedel-craft acylation reaction and Grignard reaction were conducted in the same manner as Preparation Example 1 except for using 2.2 g (1.2 molar equivalent amount) of 1-phenyl-1,3-pentadiethyl bromide represented by the following structural formula (10) instead of cinnamyl bromide (1.2 molar equivalent amount) represented by the structural formula (9), to obtain 3.46 g of a yellow powdery compound.

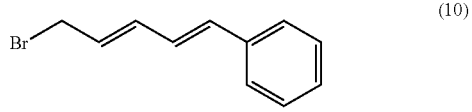

(10)

As a result of LC-MS analysis for the resultant compound, since a peak corresponding to the molecular ion [M+H]+ in which a proton was added to the aimed amine-hexatriene compound of Exemplified Compound No. 30 shown in Table 3 (calculated value of molecular weight: 491.26) was observed at 492.3. It was confirmed that the resultant compound was an amine-hexatriene compound of Exemplified Compound No. 30. Further, as the result of LC-MS analysis, it was found that the purity of the resultant amine-hexatolyene compound of the obtained Exemplified Compound No. 30 was 99.1%.

As described above, by conducting two stage reactions of Friedel-craft acylation reaction and Grignard reaction, the amine-hexatriene compound of Exemplified Compound No. 30 could be obtained without using a phosphorous reaction reagent.

EXAMPLE

Examples of the invention are to be described below.

Example 1

After adding 1 part by weight of the azo compound represented by the following structural formula (11) as a charge-generating substance to a resin solution obtained by dissolving one part by weight of a phenoxy resin (PKHH, manufactured by Union Carbide Co.) to 99 parts by weight of THF, they were dispersed by a paint shaker for 2 hours to prepare a coating solution for charge-generating layer. After coating the coating solution for charge-generating layer on aluminum of a conductive support formed by vapor depositing aluminum on the surface of a polyester film of 80 μm thickness by a baker applicator, it was dried to form a charge-generating layer of 0.3 μm thickness.

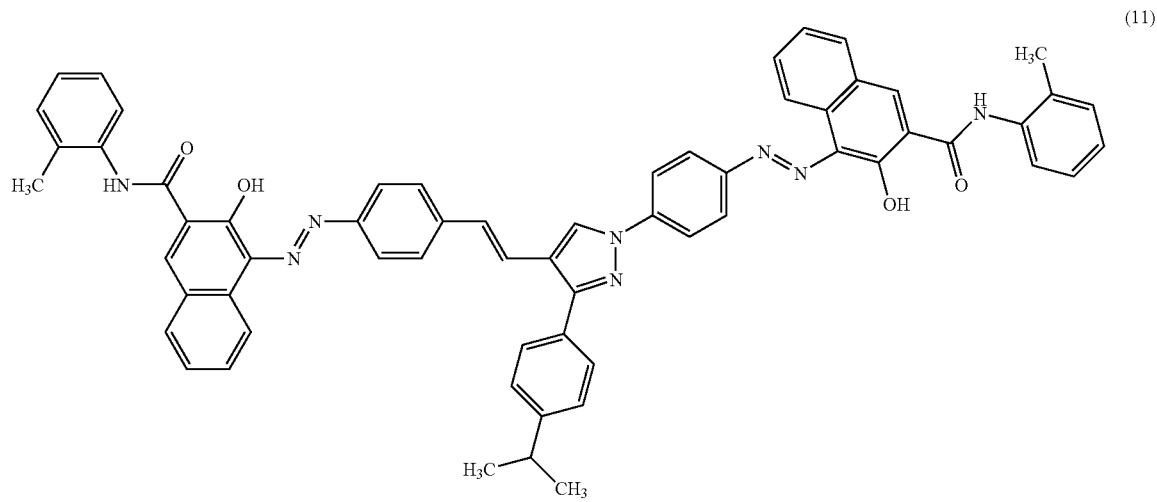

(11)

Then, 8 parts by weight of the amine-butadiene compound of Exemplified Compound No. 1 shown in Table 1 as the charge-transporting substance and 10 parts by weight of a polycarbonate resin (C-1400, manufactured by Teijin Kasei Co.) as a binder resin were dissolved in 80 parts by weight of THF to prepare a coating solution for charge transpiration layer. After coating the coating solution for charge-transporting layer on the previously formed charge-generating layer by a baker applicator, it was dried to form a charge-transporting layer of 10 μm thickness.

As described above, a lamination type electrophotographic photoreceptor of the layer constitution shown in FIG. 1 was prepared.

Examples 2, 3

Two kinds of electrophotographic photoreceptors were prepared in the same manner as in Example 1 except for using the amine-butadiene compound of Exemplified Compound No. 9 shown in Table 1 or No. 14 shown in Table 2 instead of the amine-butadiene compound of Exemplified Compound No. 1 as the charge-transporting substance.

Example 4

An electrophotographic photoreceptor was prepared in the same manner as in Example 1 except for using the amine-hexatriene compound of Exemplified Compound No. 30 shown in Table 3 instead of the amine-butadiene compound of Exemplified Compound No. 1 as the charge-transporting substance.

Comparative Example 1

An electrophotographic photoreceptor was prepared in the same manner as in Example 1 except for using Comparative Compound A represented by the following structural formula (12) instead of the amine-butadiene compound of Exemplified Compound No. 1 as the charge-transporting substance.

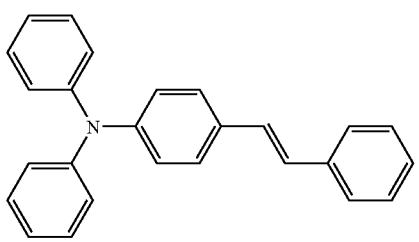

(12)

Comparative Example 2

An electrophotographic photoreceptor was prepared in the same manner as in Example 1 except for using Comparative Compound B represented by the following structural formula (13) instead of the amine-butadiene compound of Exemplified Compound No. 1 as the charge-transporting substance.

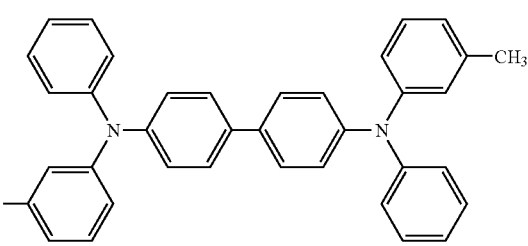

(13)

[Evaluation 1]

For each of electrophotographic photoreceptors manufactured in Examples 1 to 4 and Comparative Examples 1 and 2 described above, an ionization potential was measured by using a surface analyzer (AC-1, manufactured by Riken Keiki Co. Ltd.). Further, gold was vapor deposited on the surface of the charge-transporting layer of each of the electrophotographic photoreceptors, and the charge mobility of the charge-transporting substance was measured by a Time-of- Flight method at a room temperature and a reduced pressure. The results of the measurement are shown in Table 5. The values of the charge mobility shown in Table 5 are values when the intensity of the electric field was at 2.5×10⁵ V/cm.

TABLE 5

|  | Charge-transporting substance | Ionization potential (eV) | Charge mobility (cm²/ V · sec) |
|---|---|---|---|
| Example 1 | Exemplified Compound 1 | 5.61 | $6.7 \times 10^{-4}$ |
| Example 2 | Exemplified Compound 9 | 5.54 | $5.6 \times 10^{-4}$ |
| Example 3 | Exemplified Compound 14 | 5.57 | $5.1 \times 10^{-4}$ |
| Example 4 | Exemplified Compound 30 | 5.51 | $2.4 \times 10^{-4}$ |
| Comparative Example 1 | Comparative Compound A | 5.65 | $4.3 \times 10^{-5}$ |
| Comparative Example 2 | Comparative Compound B | 5.40 | $1.2 \times 10^{-6}$ |

It was found from the comparison between Examples 1 to 4 and Comparative Example 1 that the amine compound of the invention represented by the general formula (1) had a charge mobility higher by one digit or more than the amine-styryl compound such as Comparative Compound A as a charge-transporting substance known so far.

It was found from the comparison between Examples 1 to 4 and Comparative Example 2 that the amine compound of the invention represented by the general formula (1) had a charge mobility higher by two digits or more than the triphenylamine dimer (abbreviated as TPD) such as Comparative Compound B as a charge-transporting substance known so far.

It was found from the comparison between Examples 1 and Examples 2 to 4 that the amine-butadiene compound represented by the general formula (2) has particularly high charge mobility among the amine compounds represented by the general formula (1).

Example 5

9 parts by weight of dendritic titanium oxide (TTO-D-1, manufactured by Ishihara Sangyo Kaisha. Ltd.) surface treated with aluminum oxide (chemical formula: Al₂O₃) and zirconium dioxide (chemical formula: ZrO₂) and 9 parts by weight of a copolymer nylon resin (CM 8000, manufactured by Toray Industries Inc.) were added to a mixed solvent of 41 parts by weight of 1,3-dioxolane and 41 parts by weight of methanol, which were dispersed by using a paint shaker for 12 hours to prepare a coating solution for intermediate layer. The prepared coating solution for intermediate layer was coated by a baker applicator on a planar aluminum conductive support of 0.2 mm thickness and, dried to form an intermediate layer having a film thickness of 1 μm.

Then, 2 parts of an azo compound represented by the following structural formula (14) as a charge-generating substance was added to a resin solution obtained by dissolving one part by weight of a polyvinyl butyral resin (BX-1, manufactured by Sekisui Chemical Co. Ltd.) in 97 parts by weight of THF, which were then dispersed by a paint shaker for 10 hours to prepare a coating solution for charge-generating layer. The coating solution for charge-generating layer was coated on the previously formed intermediate layer by a baker applicator, and then dried to form a charge-generating layer having a film thickness of 0.3 μm.

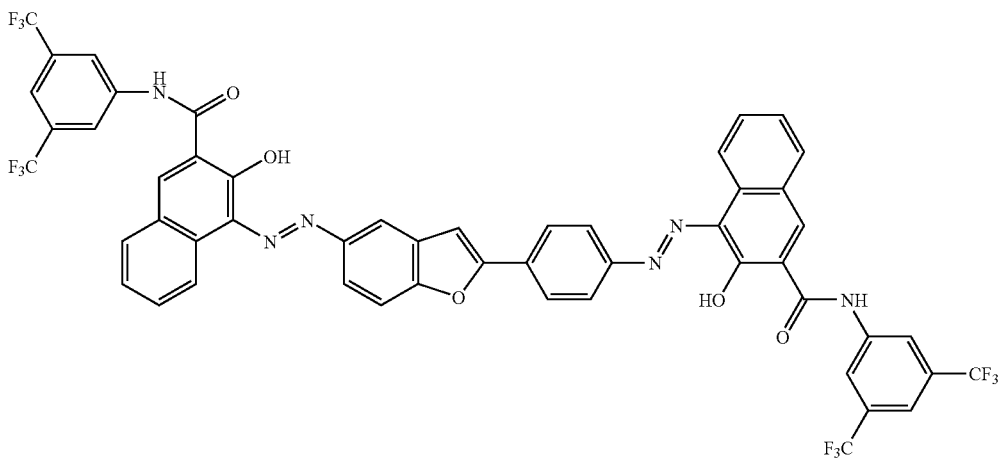

(14)

Then, 10 parts by weight of the amine-butadine compound of Exemplified Compound No. 1 shown in Table 1 as a charge-transporting substance, 14 parts by weight of a polycarbonate resin (Z200, manufactured by Mitsubishi Gas Chemical Co. Inc.) and 0.2 parts by weight of 2,6-di-t-butyl-4-methylphenol were dissolved in 80 parts by weight of THF to prepare a coating solution for charge-transporting layer. The coating solution for charge-transporting layer was coated on the previously formed charge-generating layer by a baker applicator, which was then dried to form a charge-transporting layer having a film thickness of 18 μm.

With such procedures as described above, a laminated type electrophotographic photoreceptor having a layer constitution shown in FIG. 2 was prepared.

Examples 6 and 7

Two kinds of electrophotographic photoreceptors were prepared in the same manner as in Example 5 except for using Exemplified Compound No. 9 shown in Table 1 or the amine-butadiene compound of No. 19 shown in Table 2 instead of the amine-butadiene compound of Exemplified Compound No. 1 as a charge-transporting substance.

Example 8

An electrophotographic photoreceptor was prepared in the same manner as in Example 5 except for using the amine-hexatriene compound of Exemplified Compound No. 33 shown in Table 3 instead of the amine-butadiene compound of Exemplified Compound No. 1 as a charge-transporting substance.

Comparative Examples 3 and 4

Two kinds of electrophotographic photoreceptors were prepared in the same manner as in Example 5 except for using Comparative Compound A represented by the structural formula (12) or Comparative Compound B represented by the structural formula (13) instead of the amine-butadiene compound of Exemplified Compound No. 1 as a charge-transporting substance.

Example 9

In the same manner as in Example 5, an intermediate layer having a film thickness of 1 μm was formed on a planar aluminum conductive substrate of 0.2 mm thickness.

Then, one part by weight of an azo compound represented by the structural formula (14) as a charge-generating substance, 12 parts by weight of a polycarbonate resin (Z-400, Mitsubishi Gas Chemical Co. Inc.) as a binder resin, 10 parts by weight of the amine-butadiene compound of Exemplified Compound No. 1 shown in Table 1, 5 parts by weight of 3,5-dimethyl-3',5'-di-t-butyl diphenoquinone, 0.5 parts by weight of 2,6-di-t-butyl-4-methylphenol as the charge-transporting substances, and 65 parts of THF were dispersed in a ball mill for 12 hours to prepare a coating solution for photosensitive layer. The coating solution for photosensitive layer was coated on the previously formed intermediate layer by a baker applicator, and then dried by hot blow at a temperature of 110° C. for one hour to form a photosensitive layer having a film thickness of 20 μm.

As described above, a single-layer type electrophotographic photoreceptor of the layer constitution shown in FIG. 3 was prepared.

Example 10

An electrophotographic photoreceptor was prepared in the same manner as in Example 5 except for using an X-type nonmetal phthalocyanine instead of the azo compound represented by the structural formula (14) as a charge-generating substance.

Examples 11 and 12

Two kinds of electrophotographic photoreceptors were prepared in the same manner as in Example 5 except for using an X-type nonmetal phthalocyanine instead of the azo compound represented by the structural formula (14) as a charge-generating substance and using the amine-butadiene compound of Exemplified Compound No. 13 or No. 24 shown in Table 2 instead of the amine-butadiene compound of Exemplified Compound No. 1 as a charge-transporting substance.

Example 13

An electrophotographic photoreceptor was prepared in the same manner as in Example 5 except for using an X type nonmetal phthalocyanine instead of the azo compound represented by the structural formula (14) as a charge-generating substance and using the amine-hexatriene compound of Exemplified Compound No. 36 shown in Table 3 instead of the amine-butadiene compound of Exemplified Compound No. 1 as a charge-transporting substance.

Comparative Examples 5 and 6

Two kinds of electrophotographic photoreceptors were prepared in the same manner as in Example 5 except for using an X-type nonmetal phthalocyanine instead of the azo compound represented by the structural formula (14) as a charge-generating substance and using Comparative Compound A represented by the structural formula (12) or Comparative Compound B represented by the structural formula (13) instead of the amine-butadiene compound of Exemplified Compound No. 1 as a charge-transporting substance.

[Evaluation 2]

For each of electrophotographic photoreceptors prepared in Examples 5 to 13, and Comparative Examples 3 to 6 described above, characteristics at the initial stage and after repetitive use were evaluated by using an electrostatic copy paper testing apparatus (EPA-8200, manufactured by Kabushiki Kaisha Kawaguchi Denki Seisakusho). Evaluation was effected under each of the circumstances of normal temperature/normal humidity (N/N) at a temperature of 22° C. and a relative humidity of 65% and a low temperature/low humidity (L/L) circumstance at a temperature of 5° C. and a relative humidity of 20% respectively as described below.

The surface of the photoreceptor was charged by applying a voltage at minus (−)5 kV to the photoreceptor and the surface potential of the photoreceptor at this stage was measured as a charge potential $V_0$ (V). In a case of the single layer type photoreceptor of Example 9, the surface of the photoreceptor was charged by applying a voltage at plus (+)5 kV.

Then, the exposure was applied to the charged surface of the photoreceptor. In this case, an exposure energy required for decaying the surface potential of the photoreceptor to one-half from the charge potential $V_0$ was measured as a half-decay exposure amount $E_{1/2}$ (μJ/cm$^2$), which was defined as the evaluation index for the sensitivity. Further, the surface potential of the photoreceptor at the lapse of 10 sec from the start of the exposure was measured as the residual potential $V_r$ (V), which was defined as the evaluation index for the light responsiveness. In the exposure, a white light at an exposure energy of 1 μW/cm$^2$ was used in a case of the photoreceptors of Examples 5 to 10 and Comparative Examples 3 and 4 using the azo compound represented by the structural formula (14), and a monochromatic light at a wavelength of 780 nm and at an exposure energy of 1 μW/cm$^2$ obtained by spectralization through a monochrometer was used in a case of photoreceptors of Examples 10 to 13 and Comparative Examples 5 and 6 using the X-type non-metal phthalocyanine.

The results of the measurement described above were defined as the result of measurement at the initial stage.

Then, after repeating the operation of the charging and exposure described above for 5,000 times as one cycle, the charge potential $V_0$, the half-decay exposure amount $E_{1/2}$ and the residual potential $V_r$ were measured in the same manner as that for the initial stage. The results of the measurement described above were defined as the result of measurement after repetitive use.

Table 6 shows the results of measurement in the initial stage and after repetitive use described above.

TABLE 6

| | Charge-generating substance | Charge-transporting substance | Under N/N circumstance (22° C./65% RH) | | | | | | Under L/L circumstance (5° C./20% Rh) | | | | | |
|---|---|---|---|---|---|---|---|---|---|---|---|---|---|---|
| | | | Initial stage | | | After repetitive use | | | Initial stage | | | After repetitive use | | |
| | | | $E_{1/2(\mu m)^2}$ | $V_0(V)$ | $V_r(V)$ | $E_{1/2(\mu m)^2}$ | $V_0(V)$ | $V_r(V)$ | $E_{1/2(\mu m)^2}$ | $V_0(V)$ | $V_r(V)$ | $E_{1/2(\mu m)^2}$ | $V_0(V)$ | $V_r(V)$ |
| Example 5 | Azo compound (14) | Exemplified Compound 1 | 0.16 | −581 | −18 | 0.18 | −570 | −21 | 0.17 | −582 | −23 | 0.19 | −578 | −25 |
| Example 6 | Azo compound (14) | Exemplified Compound 9 | 0.15 | −579 | −14 | 0.17 | −568 | −20 | 0.17 | −582 | −18 | 0.20 | −574 | −24 |
| Example 7 | Azo compound (14) | Exemplified Compound 19 | 0.17 | −581 | −16 | 0.19 | −572 | −19 | 0.19 | −584 | −19 | 0.21 | −578 | −21 |
| Example 8 | Azo compound (14) | Exemplified compound 33 | 0.14 | −582 | −13 | 0.17 | −571 | −21 | 0.16 | −586 | −18 | 0.19 | −574 | −23 |
| Comp. Example 3 | Azo compound (14) | Comparative Compound A | 0.19 | −571 | −35 | 0.23 | −565 | −38 | 0.21 | −576 | −43 | 0.37 | −570 | −48 |
| Comp. Example 4 | Azo compound (14) | Comparative Compound B | 0.21 | −584 | −42 | 0.24 | −570 | −45 | 0.23 | −588 | −51 | 0.51 | −576 | −64 |
| Example 9 | Azo compound (14) | Exemplified Compound 1 | 0.27 | 558 | 24 | 0.30 | 536 | 28 | 0.29 | −560 | 28 | 0.31 | 545 | 32 |
| Example 10 | X-type non metal phthalocyanine | Exemplified Compound 1 | 0.14 | −578 | −8 | 0.16 | −562 | −17 | 0.17 | −582 | −11 | 0.19 | −574 | −18 |
| Example 11 | X-type non metal phthalocyanine | Exemplified Compound 13 | 0.15 | −571 | −10 | 0.17 | −565 | −16 | 0.17 | −577 | −13 | 0.20 | −571 | −20 |
| Example 12 | X-type non metal phthalocyanine | Exemplified Compound 24 | 0.13 | −576 | −9 | 0.16 | −564 | −18 | 0.16 | −583 | −13 | 0.19 | −578 | −21 |
| Example 13 | X-type non metal phthalocyanine | Exemplified Compound 36 | 0.14 | −581 | −12 | 0.16 | −569 | −20 | 0.18 | −581 | −17 | 0.21 | −572 | −22 |
| Comp. Example 5 | X-type non metal phthalocyanine | Comparative Compound A | 0.16 | −579 | −25 | 0.19 | −565 | −29 | 0.19 | −586 | −33 | 0.23 | −578 | −41 |
| Comp. Example 6 | X-type non metal- phthalocyanine | Comparative Compound B | 0.19 | −574 | −30 | 0.22 | −566 | −42 | 0.23 | −587 | −51 | 0.45 | −568 | −59 |

From comparison between Examples 5 to 8 and Comparative Examples 3 and 4, and comparison between Examples 10 to 13 and the Comparative Examples 5 and 6, it was found that photoreceptors of Examples 5 to 8 and 10 to 13 using the amine compound of the invention represented by the general formula (1) as the charge-transporting substance were highly sensitive with smaller half decay exposure amount $E_{1/2}$ and excellent in the light responsiveness having smaller absolute value of the residual potential $V_r$ both under the N/N circumstance and the L/L circumstance compared with the photoreceptors of Comparative Compounds 3 to 6 using the Comparative Compounds A or B as the charge-transporting substance.

Further, from Table 6, it was found that the photoreceptors of Examples 5 to 13 using the amine compound of the invention represented by the general formula (1) as the charge-transporting substance were excellent in the circumstantial stability showing less difference between the result of measurement under the N/N circumstance and the result of measurement under the L/L circumstance and had sufficient sensitivity and light responsiveness even under the L/L circumstance, whereas the photoreceptors of Comparative Examples 3 to 6 using Comparative Compound A or B as the charge-transporting substance showed larger difference between the result of the measurement under the N/N circumstance and the result of the measurement under the L/L circumstance and could not obtain sufficient sensitivity and light responsiveness under the L/L circumstance. Further, it was found that the photoreceptors of Examples 5 to 13 were excellent in the electrical durability showing smaller difference between the result of the measurement in the initial stage and the result of the measurement after repetitive use both under the N/N circumstance and the L/L circumstance.

Further, from the comparison between Examples 5 to 8 and the Example 9, it was found that the lamination type photoreceptor of Examples 5 to 8 had higher sensitivity showing smaller half-decay exposure amount $E_{1/2}$ and were excellent in the light responsiveness showing smaller absolute value of residual potential $V_r$ than those of the single layered type photoreceptor of Example 9.

Example 14

9 parts by weight of dendritic titanium oxide (TTO-D-1, manufactured by Ishihara Sangyo Kaisha. Ltd.) surface of which was treated with aluminum oxide ($Al_2O_3$) and zirconium dioxide ($ZrO_2$) and 9 parts by weight of a copolymer nylon resin (CM 8000, manufactured by Toray Industries Inc.) were added to a mixed solvent of 41 parts by weight of 1,3-dioxolane and 41 parts by weight of methanol, which were then dispersed by using a paint shaker for 8 hours to prepare a coating solution for intermediate layer. The prepared coating solution for intermediate layer was filled in a coating vessel, a cylindrical aluminum conductive support of 40 mm diameter and 340 mm length was immersed therein and then pulled up, which was dried to form an intermediate layer having a film thickness of 1.0 µm on the conductive support.

Then, 2 parts by weight of an oxotitanium phthalocyanine (general formula (A), $R^7$, $R^8$, $R^9$ and $R^{10}$ each represents a hydrogen atom) having a crystal structure showing a distinct diffraction peak at least at a Bragg angle $2\theta$ (error: $2°\pm0.2°$) of $27.2°$ in an X-ray diffraction spectrum relative to Cu—Kα characteristic X-rays (wavelength: 1.54 Å) as a charge-generating substance, one part by weight of a polyvinyl butylal resin (Esrec BM-S, manufactured by Sekisui Chemical Co. Ltd.) and 97 parts by weight of methyl ethyl ketone were mixed, dispersed by a paint shaker to prepare a coating solution for charge-generating layer. The coating solution for charge-generating layer was coated on the intermediate layer by a dip coating method similar to that for the previously formed intermediate layer and dried to form a charge-generating layer having a film thickness of 0.4 µm.

Then, 10 parts by weight of the amine-butadiene compound of the Exemplified Compound No. 1 shown in Table 1 as a charge-transporting substance, 20 parts by weight of a polycarbonate resin (Yupiron Z200, manufactured by Mitsubishi Engineering Plastics Co. Ltd.) as a binder resin, one part by weight of 2,6-di-t-butyl-4-methylphenyl and 0.004 parts by weight of dimethyl polysiloxane (KF-96, manufactured by Shin-Etsu Chemical Co. Ltd.) were dissolved in 110 parts by weight of THF to prepare a coating solution for charge-transporting layer. The solution for the charge-transporting layer was coated on the previously formed charge-generating layer by a dip-coating method similar to that for the previously formed intermediate layer, and then dried at 110° C. for one hour to form a charge-transporting layer having a film thickness of 23 µm.

As described above, a lamination type electrophotographic photoreceptor of the layer constitution shown in FIG. 2 was prepared.

Examples 15 and 16

Two kinds of electrophotographic photoreceptors were prepared in the same manner as in Example 14 except for using the amine-butadiene compound of the Exemplified Compound No. 19 shown in Table 2 or the amine-hexatriene compound of Exemplified Compound No. 30 shown in Table 3 instead of the amine-butadiene compound of the Exemplified Compound No. 1 as a charge-transporting substance.

Comparative Example 7

An electrophotographic photoreceptor was prepared in the same manner as in Example 14 except for using the comparative compound B represented by the structural formula (13) instead of the amine-butadiene compound of the Exemplified Compound No. 1 as a charge-transporting substance.

Comparative Example 8

An electrophotographic photoreceptor was prepared in the same manner as in Example 14 except for using Comparative Compound C represented by the following structural formula (15) instead of the amine-butadiene compound of Exemplified Compound No. 1 as a charge-transporting substance.

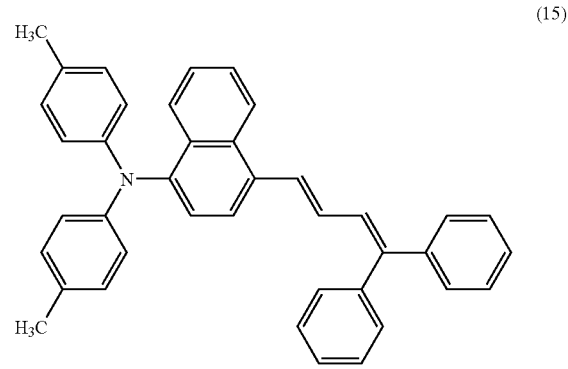

(15)

Example 17

An electrophotographic photoreceptor was prepared in the same manner as in Example 14 except for determining the amount of the polycarbonate resin as a binder resin to 25 parts by weight upon formation of the charge-transporting layer.

Examples 18 and 19

Two kinds of electrophotographic photoreceptors were prepared in the same manner as in Example 14 except for determining the amount of the polycarbonate resin as the binder resin to 25 parts by weight and using the amine-butadiene compound of Exemplified Compound No. 22 shown in Table 2 or the amine-hexatriene compound of Exemplified Compound No. 35 shown in Table 3 instead of the amine-butadiene compound of Exemplified Compound No. 1 as a charge-transporting substance upon formation of the charge-transporting layer.

Comparative Example 9

An electrophotographic photoreceptor was prepared in the same manner as in Example 14 except for determining the amount of the polycarbonate resin as a binder resin to 25 parts by weight and using the comparative compound B represented by the structural formula (13) instead of the amine-butadiene compound of Exemplified Compound No. 1 as a charge-transporting substance upon formation of the charge-transporting layer.

Comparative Example 10

An electrophotographic photoreceptor was prepared in the same manner as in Example 14 except for determining the amount of the polycarbonate resin as a binder resin to 25 parts by weight and using the comparative compound C represented by the structural formula (15) instead of the amine-butadiene compound of Exemplified Compound No. 1 as a charge-transporting substance upon formation of the charge-transporting layer.

Example 20

An electrophotographic photoreceptor was prepared in the same manner as in Example 14 except for determining the amount of the polycarbonate resin as a binder resin to 10 parts by weight upon formation of the charge-transporting layer.

Comparative Example 11

An electrophotographic photoreceptor was prepared in the same manner as in Example 14 except for determining the amount of the polycarbonate resin as a binder resin to 10 parts by weight and using comparative compound C represented by the structural formula (15) instead of the amine-butadiene compound of Exemplified Compound No. 1 as a charge-transporting substance upon formation of the charge-transporting layer.

Reference Example

An electrophotographic photoreceptor was prepared in the same manner as in Example 14 except for determining the amount of the polycarbonate resin as a binder resin to 31 parts by weight upon formation of the charge-transporting layer.

However, since a coating solution for charge-transporting layer in which a polycarbonate resin was completely dissolved therein could not be prepared, with the same amount of THF as that in Example 14, THF was added to prepare a coating solution for charge-transporting layer in which the polycarbonate resin was completely dissolved therein, and the charge-transporting layer was formed by using the same.

However, clouding due to the brushing phenomenon was resulted at the longitudinal end of the cylindrical photoreceptor and characteristic evaluation could not be conducted. It is considered that the brushing phenomenon is attributable to the excess amount of the solvent in the coating solution for charge-transporting layer.

[Evaluation 3]

Each of the photoreceptors manufactured in Examples 14 to 20 and Comparative Examples 7 to 11 described above was mounted on a test copying machine modified from a commercially available digital copying machine (AR-C150, manufactured by Sharp Corp.) at a printing speed of 117 mm/sec, and the printing resistance and the circumstantial stability for each of the photoreceptors were evaluated as described below. The digital copying machine Ar-C150 is a negative charging type image forming apparatus that conducts charging to the surface of the photoreceptor by a negatively charging process.

<Printing Resistance>

After forming test images of a predetermined pattern to 40,000 sheets of recording paper by using the test copying machine, the mounted photoreceptor was taken out, thickness d1 of the photosensitive layer was measured to determine the difference between the value (d1) and the thickness d0 for the prepared photosensitive layer as a film reduction amount $\Delta d$ ($=d0-d1$), which was defined as the evaluation index for the printing resistance. Measurement for the film thickness was conducted by an instantaneously multi-light measuring system MCPD-1100 (manufactured by Otsuka Denshi Co.) by a light interference method.

<Circumstantial Stability>

The developing device was detached from the test copying machine and, instead, a surface potential meter (CATE751, manufactured by Gentec Co.) is provided to the developing portion. Using the copying machine, the surface potential of the photoreceptor in a case not exposing the laser light was measured as the charge potential V0 (V) under a normal temperature/normal humidity (N/N) circumstance at a temperature of 22° C. and a relative humidity of 65% (N/N). Further, the surface potential of the photoreceptor after applying the laser light exposure was measured as an exposure potential VL (V), which was determined as an exposure potential $VL_N$ under the N/N circumstance. It was evaluated that the chargeability was more excellent as the absolute value for the charging potential V0 was larger and the light responsiveness was evaluated to be excellent as the absolute value for the exposure potential $VL_N$ was smaller.

Further, under a Low temperature/Low humidity (L/L) circumstance at a temperature of 5° C. and at a relative humidity of 20%, the exposure potential VL(V) was measured in the same manner as under the N/N circumstance, and it was defined as the exposure potential $VL_L$ under the L/L circumstance. The absolute value for the difference between the exposure potential $VL_N$ under the N/N circumstance and the exposure potential $VL_N$ under the L/L circumstance was determined as: potential fluctuation $\Delta VL (=|VL_L-VL_N|)$. As the potential fluctuation $\Delta VL$ was smaller, it was judged to be more excellent in view of the circumstantial stability.

The result of the evaluation for them are shown in Table 7.

TABLE 7

| | Charge-transporting substance | Charge-transporting substance/ binder resin | Film reduction amount $\Delta d$ (μm) | N/N-potential characteristic V0(V) | N/N-potential characteristic $VL_N$(V) | L/L-potential fluctuation $\Delta VL$(V) |
|---|---|---|---|---|---|---|
| Example 14 | Exemplified Compound 1 | 10/20 | 3.4 | −541 | −38 | 23 |
| Example 15 | Exemplified Compound 19 | 10/20 | 3.6 | −528 | −34 | 19 |
| Example 16 | Exemplified Compound 30 | 10/20 | 3.7 | −536 | −36 | 24 |
| Comp. Example 7 | Comparative Compound B | 10/20 | 4.4 | −520 | −84 | 69 |
| Comp. Example 8 | Comparative Compound C | 10/20 | 4.9 | −520 | −34 | 24 |
| Example 17 | Exemplified Compound 1 | 10/25 | 1.9 | −531 | −47 | 29 |
| Example 18 | Exemplified Compound 22 | 10/25 | 2.1 | −527 | −44 | 28 |
| Example 19 | Exemplified Compound 35 | 10/25 | 2.3 | −533 | −41 | 31 |
| Comp. Example 9 | Comparative Compound B | 10/25 | 3.2 | −508 | −92 | 78 |
| Comp. Example 10 | Comparative Compound C | 10/25 | 3.7 | −511 | −55 | 32 |
| Example 20 | Exemplified Compound 1 | 10/10 | 6.9 | −517 | −17 | 9 |
| Comp. Example 11 | Comparative Compound C | 10/10 | 9.1 | −521 | −21 | 13 |
| Reference Example | Exemplified Compound 1 | 10/31 | — | — | — | — |

From comparison between Examples 14 to 16 and the Comparative Example 7 and comparison between Examples 17 to 19 and Comparative Example 9 it was found that the photoreceptors of Examples 14 to 19 using the amine compound of the invention represented by the general formula (1) as the charge-transporting substance had smaller absolute value of the exposure potential $VL_N$ under the N/N circumstance and were excellent in the light responsiveness even in a case of adding the binder resin at a high ratio compared with the photoreceptors of Comparative Examples 7 and 9 and the Comparative Compound B as the charge-transporting substance. Further, it was found that the photoreceptors of Examples 14 to 19 had smaller values of the potential fluctuation $\Delta VL$ and were excellent in the circumstantial stability and showed a sufficient light responsiveness even under the L/L circumstance compared with the photoreceptors of Comparative Examples 7 and 9.

Further, from comparison between Examples 14 to 16 and the Comparative Example 8, comparison between Examples 17 to 19 and Comparative Example 10, and the comparison between Example 20 and Comparative Example 11, it was found that the photoreceptors of Examples 14 to 20 using the amine compound of the invention represented by the general formula (1) as the charge-transporting substance had less film reduction amount $\Delta d$ and were excellent in the printing resistance than the photoreceptors of Comparative Examples 8, 10 and 11 using Comparative Compound C as the charge-transporting substance, in a case where the ratio between the weight of the charge-transporting substance and the weight of the binder resin (charge-transporting substance/binder resin) was equal. It is estimated that the difference is attributable to the high mechanical strength of the amine compound per se of the invention represented by the general formula (1) contained in the photosensitive layer of the photoreceptors of the examples 14 to 20. That is, since the amine compound of the invention represented by the general formula (1) has 1-substitution (=CH—Ar$^3$) as the substitution pattern for the multiple bond terminal portion, a stacking structure of an ideal stacking state in which molecules are packed densely is attained. Accordingly, the mechanical strength of the amine compound represented by the general formula (1) is high and it is considered that excellent wear resistance characteristic was provided to the photosensitive layer and the printing resistance of the photosensitive layer was enhanced by the incorporation of the amine compound represented by the general formula (1) in the photosensitive layer.

Further, there was no substantial difference in the electric characteristic between the photoreceptors of Examples 14 to 20 and the photoreceptors of Comparative Examples 8, 10, and 11 in a case where the ratio of the weight of the charge-transporting substance and the weight of the binder resin (charge-transporting substance/binder resin) was 10/20 or 10/10, but, when Examples 17 to 19 and Comparative Example 10 with a ratio of charge-transporting substance/binder resin of 10/25 were compared, it was found that the photoreceptors of Examples 17 to 19 had smaller absolute value of exposure potential $VL_N$ under the N/N circumstance and were more excellent in the light responsiveness than the photoreceptor of Comparative Example 10. In view of this, it is estimated that the amine compound of the invention represented by the general formula (1) has higher charge-transporting ability than that of the Comparative Compound C.

Further, it was found from Comparison between Examples 14 to 19 and Example 20 that the photoreceptors of Examples 14 to 19 with a weight ratio A/B of the weight A of the amine compound represented by general formula (1) and the weight B of the binder resin within a range from 10/30 to 10/12 had less film reduction amount $\Delta d$ and higher printing resistance than the photoreceptor of Example 20 with the ratio A/B in excess of 10/12 and at a lower ratio of the binder resin.

As described above, it was found that the amine compound of the invention represented by the general formula (1), particularly, the amine, butadiene compound represented by the general formula (2) has a high charge-transporting ability.

Further, an electrophotographic photoreceptor excellent in the electric characteristics, the circumstantial stability, and the electrical and mechanical durability can be obtained by incorporation of the amine compound of the invention represented by the general formula (1) as the charge-transporting substance in the photosensitive layer.

Further, by the use of the amine compound of the invention represented by the general formula (1) as the charge-transporting substance, it is possible to increase the ratio of the binder resin with the ratio of the weight of the charge-transporting substance and the weight of the binder resin (charge-transporting substance/binder resin) in the charge-transporting layer of 10/30 or more and 10/12 or less without deteriorating the light responsiveness, thereby improving the printing resistance of the charge-transporting layer.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An amine compound represented by the following general formula (1)

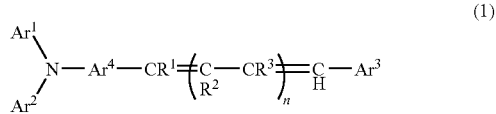

in which Ar$^1$, Ar$^2$ and Ar$^3$ each represents an aryl group which may have a substituent, or a monovalent heterocyclic ring residue which may have a substituent, Ar$^4$ is

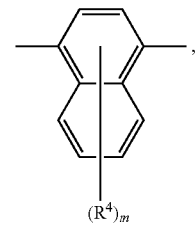

in which R$^4$ represents an alkyl group which may have a substituent, an alkoxy group which may have a substituent, a dialkylamino group represented by —NR$^5$ R$^6$ (R$^5$ and R$^6$ each represents an alkyl group which may have a substituent), an aryl group which may have a substituent, a halogen atom or a hydrogen atom; m represents an integer of from 1 to 6, when m is 2 or more, a plurality of R$^4$ may be identical with or different fro each other, and may bond with each other to form a ring structure, R$^1$ represents an alkyl group which may have a substituent, an aryl group which may have a substituent, a monovalent heterocyclic ring residue which may have a substituent, or an aralkyl group which may have a substituent, $R^2$ and $R^3$ each represents a hydrogen atom, an alkyl group which may have substituent, an aryl group which may have a substituent, a monovalent heterocyclic ring residue which may have a substituent, or an aralkyl group which may have substituent, n represents an integer of 1 to 2, when n represents 2, two $R^2$ may be identical with or different from each other, and two $R^3$ may be identical with or different from each other.

2. The amine compound of claim 1, wherein the amine compound is an amine-butadeine compound represented by the general formula (2),

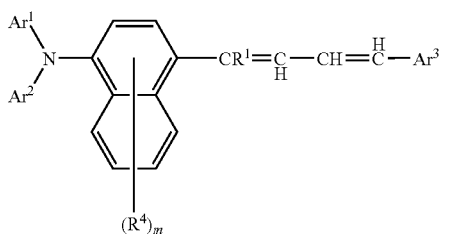

(2)

in which $R^4$ represents an alkyl group which may have a substituent, an alkoxy group which may have a substituent, a dialkylamino group represented by —$NR^5R^6$ ($R^5$ and $R^6$ each represents an alkyl group which may have a substituent), an aryl group which may have a substituent, a halogen atom or a hydrogen atom; m represents an integer of from 1 to 6, when m is 2 or more, a plurality of $R^4$ may be identical with or different from each other, and may bond with each other to form a ring structure, $Ar^1$, $Ar^2$, $Ar^3$ and $R^1$ have the same meanings as those in the general formula (1).

3. An electrophotographic photoreceptor comprising:
a conductive support made of a conductive material; and
a photosensitive layer provided on the conductive support and containing a charge-generating substance and a charge-transporting substance,
wherein the charge-transporting substance contains the amine compound of claim 1.

4. The electrophotographic photoreceptor of claim 3, wherein the charge-generating substance contains an oxotitanium phthalocyanine compound.

5. The electrophotographic photoreceptor of claim 4, wherein the oxotitanium phthalocyanine compound is an oxotitanium phthalocyanine compound having a crystal stucture showing a distinct diffraction peak at least at a Bragg angle 2θ(error: 2θ±0.2°) of 27.2° in an X-rays diffraction spectrum relative to Cu—Kα characteristic X-ray (wavelength: 1.54 Å).

6. The electrpohotographic photoreceptor of claim 3, wherein the photosensitive layer comprises a lamination of a charge-generating layer containing the charge-generating substance and a charge-transporting layer containing the charge-transporting substance.

7. The electrophotographic photoreceptor of claim 6, wherein the charge-transporting layer further contains a binder resin, and the ratio A/B between weight A for the amine compound represented by the general formula (1) and weight B for the binder resin in the charge-transporting layer is 10/30 or more and 10/12 or less.

8. The electrophotographic photoreceptor of claim 3, wherein an intermediate layer is further present between the conductive support and the photosensitive layer.

9. An image forming apparatus comprising:
the electrophotographic photoreceptor of claim 3;
charging means for charging the electrophotographic photoreceptor;
exposure means for applying exposure to the charged electrophotographic photoreceptor and
developing means for developing an electrosatic latent image formed by exposure.

10. An amine compound represented by the following general formula (1)

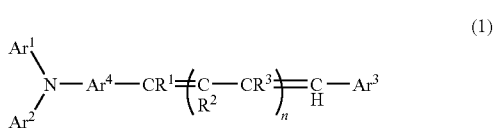

(1)

in which $Ar^1$, $Ar^2$ and $Ar^3$ each represents an aryl group which may have a substituent, or a monovalent heterocyclic ring residue which may have a substituent; $Ar^4$ represents 1,4-naphthylene, pyrenylene or 4,4'-biphenylene, which may have a substituent selected from an alkyl group, a haloalkyl group, an alkenyl group, an alkoxy group, an alkylamino group, a dialkyl amino group, a halogen atom, an aryloxyy group, and an arylthio group; $R^1$ represents an alkyl group which may have a substituent, an aryl group which may have a substituent, a monovalent heterocyclic ring residue which may have a substituent, or an aralkyl group which may have substituent; $R^2$ and $R^3$ each represents a hydrogen atom, an alkyl group which may have a substituent, an aryl group which may have a substituent, a monovalent heterocyclic ring residue which may have a substituent, or an aralkyl group which may have a substituent; n represents an integer of 1 or 2; when n represents 2, two $R^2$ may be identical with or different from each other, and two $R^3$ may be identical with or different from each other.

11. An electrophotographic photoreceptor comprising:
a conductive support made of a conductive material; and
a photosensitive layer provided on the conductive support and containing a charge-generating substance and a charge-transporting substance,
wherein the charge-transporting substance contains the amine compound of claim 10.

12. The electrophotographic photoreceptor of claim 11, wherein the charge-generating substance contains an oxotitanium phthalocyanine compound.

13. The electrophotographic photoreceptor of claim 12, wherein the oxotitanium phthalocyanine compound is an oxotitanium phthalocyanine compound having a crystal structure showing a distinct diffraction peak at least at a Bragg angle 2θ(error: 2θ±0.2°) of 27.2° in an X-rays diffraction spectrum relative to Cu—Kα characteristic X-ray (wavelength: 1.54 Å).

14. The electrophotographic photoreceptor of claim 11, wherein the photosensitive layer comprises a lamination of a charge-generating layer containing the charge-generating substance and a charge-transporting layer containing the charge-transporting substance.

15. The electrophotographic photoreceptor of claim 14, wherein the charge-transporting layer further contains a binder resin, and the ratio A/B between weight A for the amine compound represented by the general formula (1) and weight B for the binder resin in the charge-transporting layer is 10/30 or more and 10/12 or less.

16. The electrophotographic photoreceptor of claim 11, wherein an intermediate layer is further present between the conductive support and the photosensitive layer.

17. An image forming apparatus comprising:
the electrophotographic photoreceptor of claim 11;
charging means for charging the electrophotographic photoreceptor;
exposure means for applying exposure to the charged electrophotographic photoreceptor and
developing means for developing an electrostatic; latent image formed by exposure.

18. An amine compound selected from the group consisting of

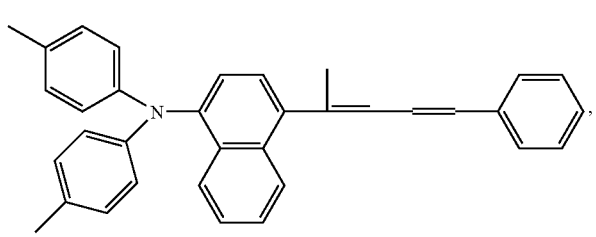
(1)

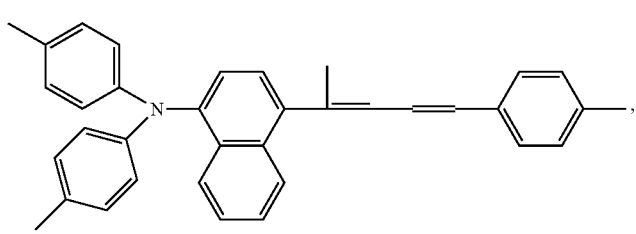
(2)

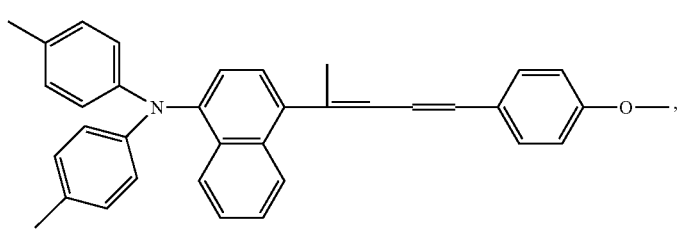
(3)

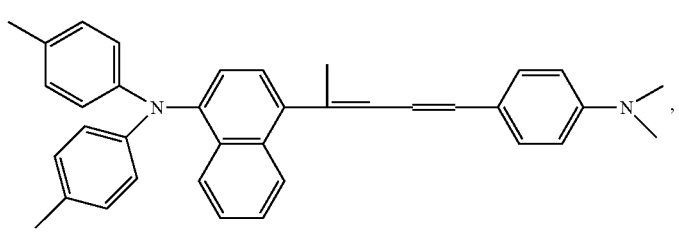
(4)

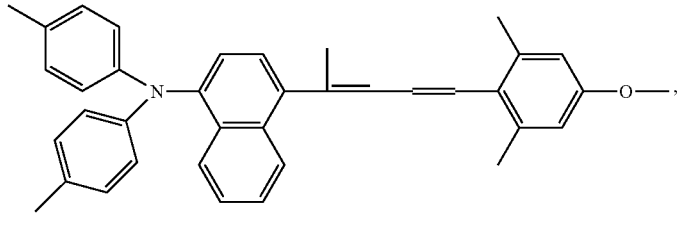
(5)

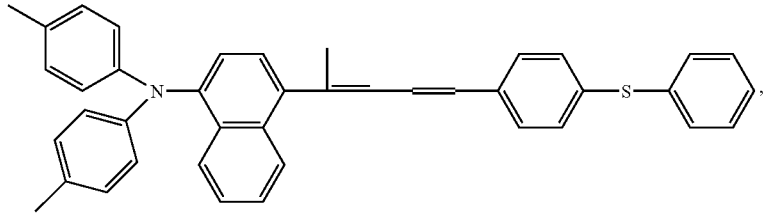
(6)

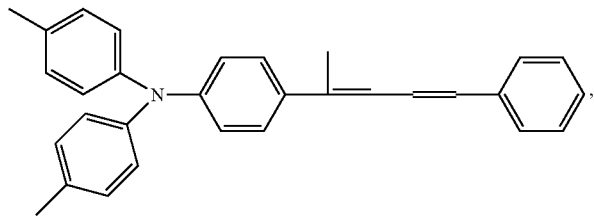
(7)
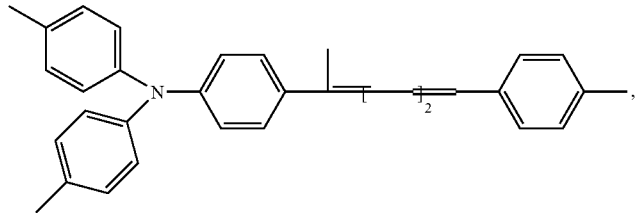
(8)
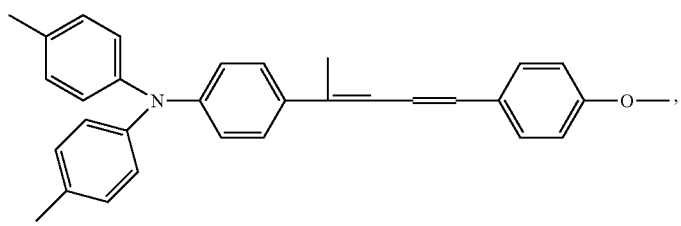
(9)
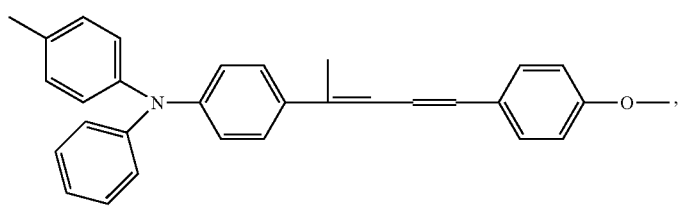
(10)
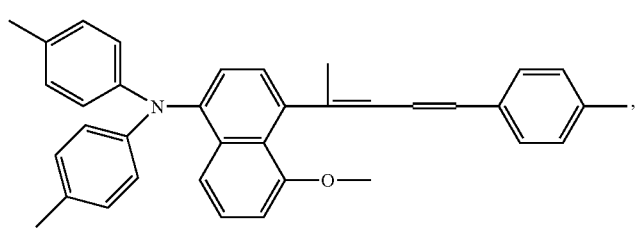
(11)
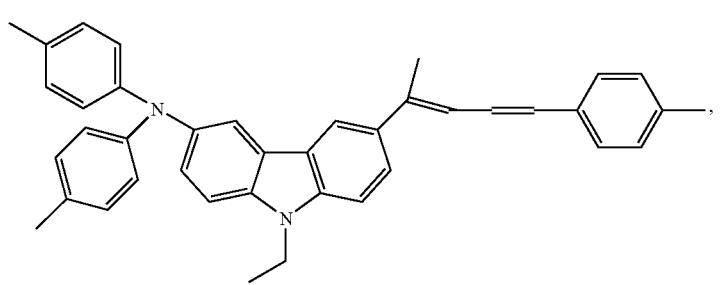
(12)

-continued
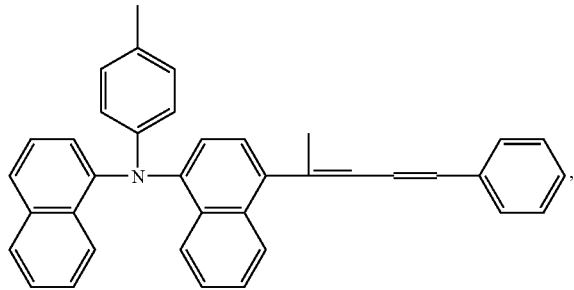
(13)
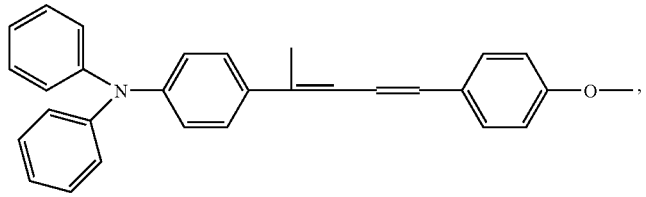
(14)
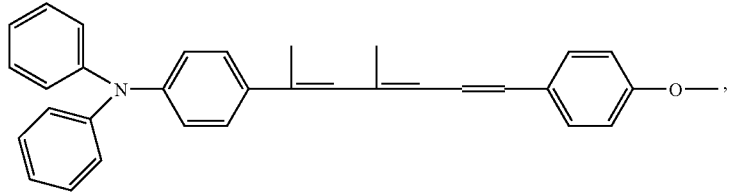
(15)
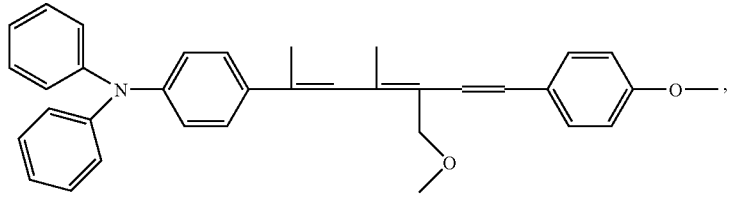
(16)
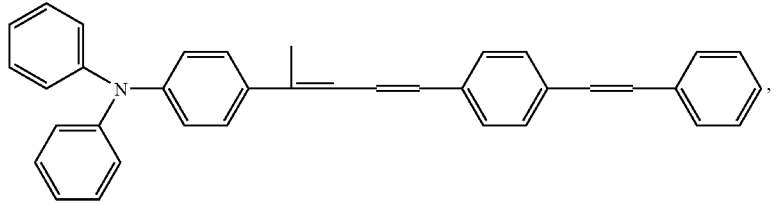
(17)
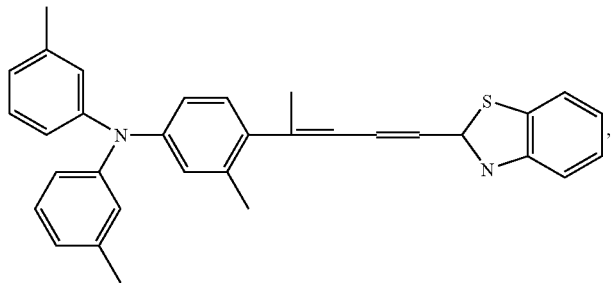
(18)

-continued
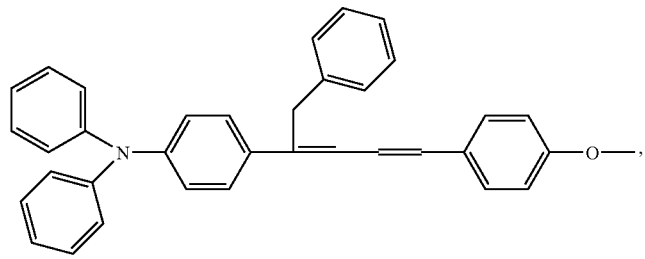
(19)
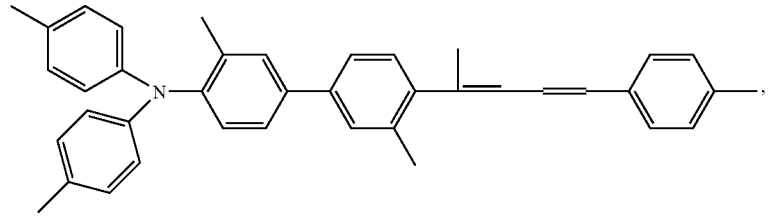
(20)
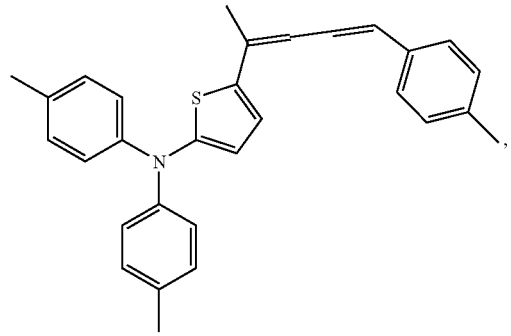
(21)
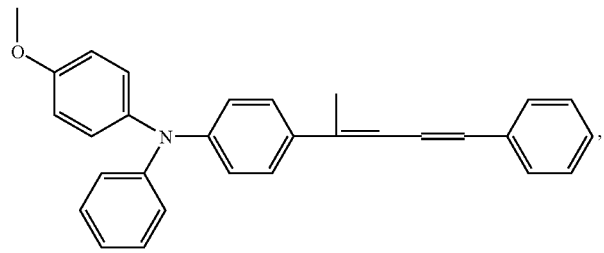
(22)
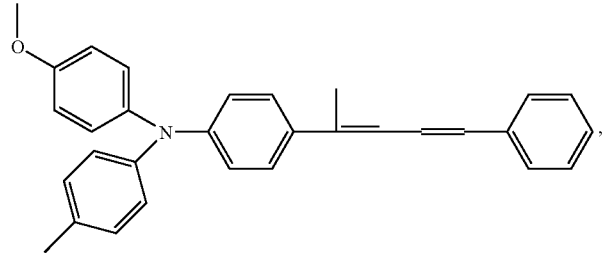
(23)
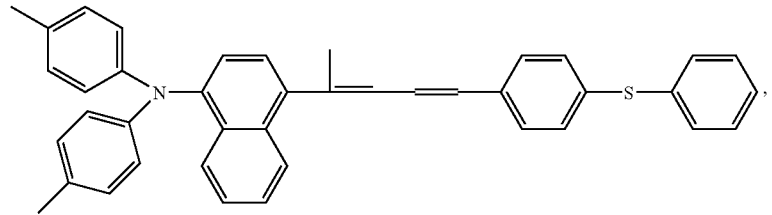
(24)

-continued
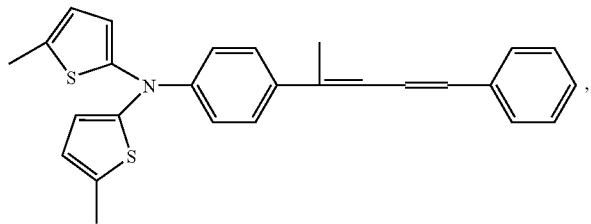
(25)
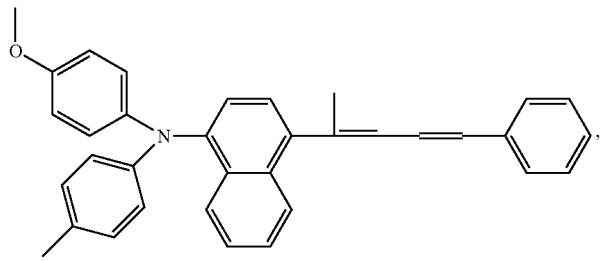
(26)
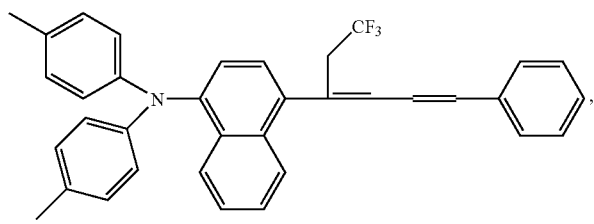
(27)
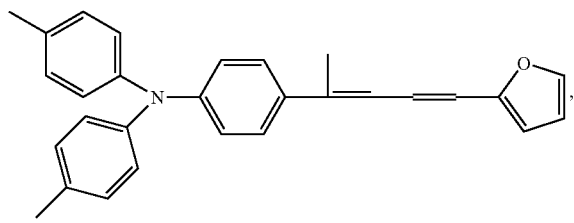
(28)
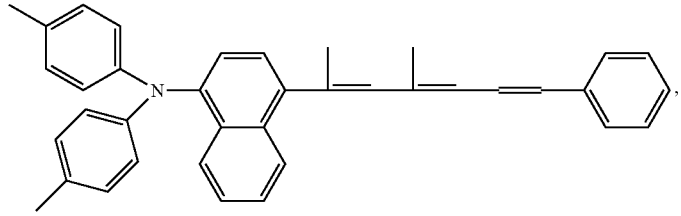
(29)
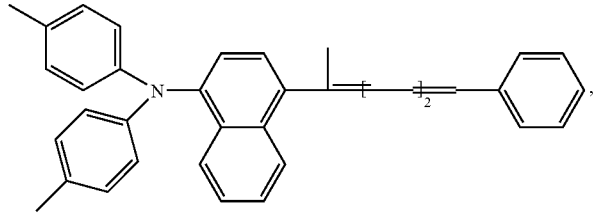
(30)
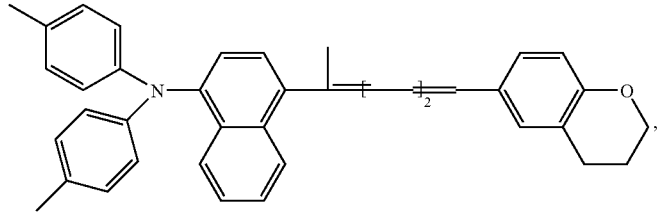
(31)

-continued
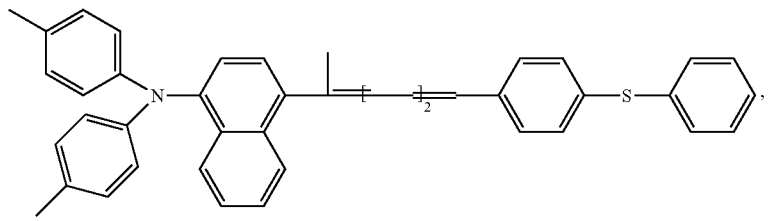
(32)
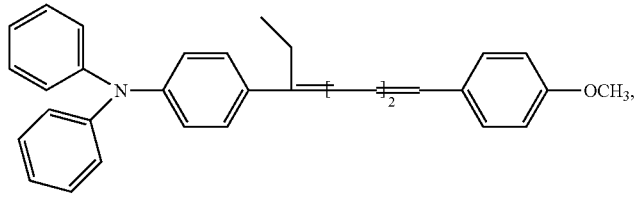
(33)
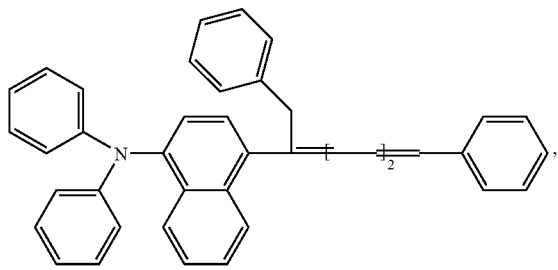
(34)
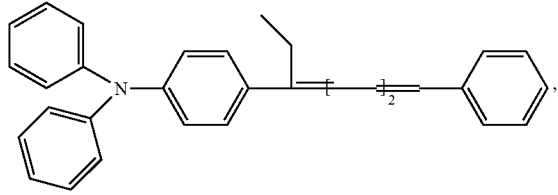
(35)
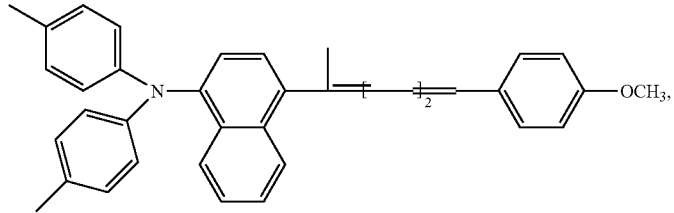
(36)
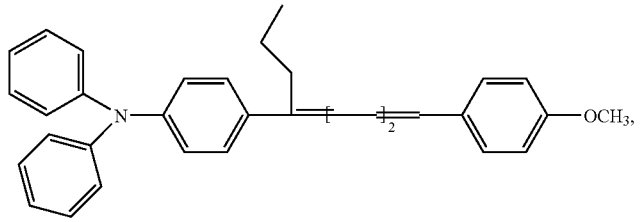
(37)
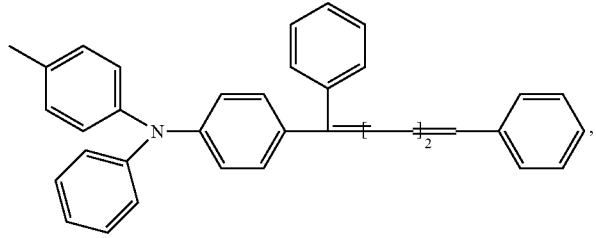
(38)

-continued

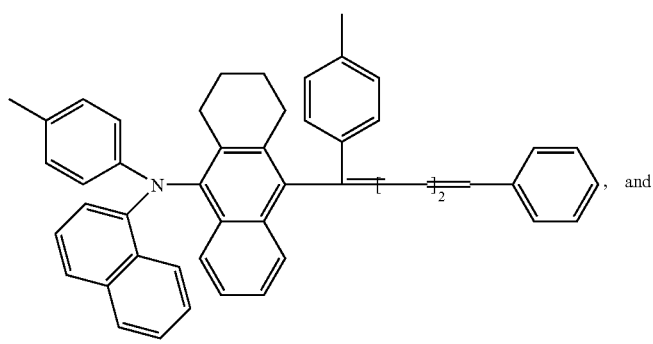, and (39)

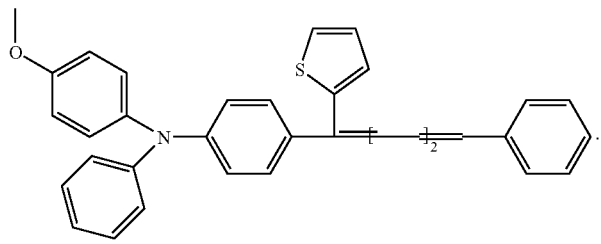.

(40)

19. An electrophotographic photoreceptor comprising:
a conductive support made of a conductive material; and
a photosensitive layer provided on the conductive support and containing a charge-generating substance and a charge-transporting substance,
wherein the charge-transporting substance contains the amine compound of claim 18.

20. The electrophotographic photoreceptor of claim 19, wherein the charge-generating substance contains an oxotitanium phthalocyanine compound.

21. The electrophotographic photoreceptor of claim 20, wherein the oxotitanium phthalocyanine compound is an oxotitanium phthalocyanine Bragg angle 2θ(error: 2θ±0.2°) of 27.2° in an X-rays diffraction spectrum relative to Cu—Kα characteristic X-ray (wavelength: 1.54 Å).

22. The electrophotographic photoreceptor of claim 19, wherein the photosensitive layer comprises a lamination of a charge-generating layer containing the charge-generating substance and a charge-transporting layer containing the charge-transporting substance.

23. The electrophotographic photoreceptor of claim 22, wherein the charge-transporting layer further contains a binder resin, and the ratio A/B between weight A for the amine compound represented by the general formula (1) and weight B for the binder resin in the charge-transporting layer is 10/30 or more and 10/12 or less.

24. The electrophotographic photoreceptor of claim 19, wherein an intermediate layer is further present between the conductive support and the photosensitive layer.

25. An image forming apparatus comprising:
the electrophotographic photoreceptor of claim 19;
charging means for charging the electrophotographic photoreceptor;
exposure means for applying exposure to the charged electrophotographic photoreceptor and
developing means for developing an electrostatic latent image formed by exposure.

* * * * *